(12) United States Patent
Beatty et al.

(10) Patent No.: US 12,145,901 B1
(45) Date of Patent: Nov. 19, 2024

(54) PROCESS FOR PREPARING TETRALIN COMPOUNDS

(71) Applicant: ARCUS BIOSCIENCES, INC., Hayward, CA (US)

(72) Inventors: Joel Worley Beatty, San Mateo, CA (US); Samuel Lawrie Drew, Millbrae, CA (US); Matthew Epplin, San Francisco, CA (US); Jeremy Fournier, Fremont, CA (US); Balint Gal, Hayward, CA (US); Karl T. Haelsig, Berkeley, CA (US); Clayton Hardman, San Francisco, CA (US); Jaroslaw Kalisiak, Newark, CA (US); Kenneth Victor Lawson, San Francisco, CA (US); Manmohan Reddy Leleti, Dublin, CA (US); Artur Karenovich Mailyan, Livermore, CA (US); Guillaume Mata, Berkeley, CA (US); Brandon Reid Rosen, San Mateo, CA (US); Zhang Wang, Foster City, CA (US); Kai Yu, Hayward, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 0 days.

(21) Appl. No.: 17/932,688

(22) Filed: Sep. 16, 2022

Related U.S. Application Data

(60) Provisional application No. 63/245,287, filed on Sep. 17, 2021.

(51) Int. Cl.
C07C 317/32 (2006.01)
B01J 23/46 (2006.01)
(Continued)

(52) U.S. Cl.
CPC ......... *C07C 317/32* (2013.01); *B01J 31/1805* (2013.01); *B01J 31/2295* (2013.01);
(Continued)

(58) Field of Classification Search
CPC ............ B01J 2231/643; B01J 2531/821; B01J 2531/824; B01J 31/1805; B01J 31/2295;
(Continued)

(56) References Cited

U.S. PATENT DOCUMENTS 9,796,697 B2    10/2017   Wehn et al.
11,407,712 B2 *  8/2022   Beatty .................. C07C 255/57
(Continued)

FOREIGN PATENT DOCUMENTS

CN     109776607 A    5/2019
CN     111303053 A    6/2020
(Continued)

OTHER PUBLICATIONS

Noyori et al. Acc. Chem. Res. 1997, 30, 97-102. (Year: 1997).*
(Continued)

*Primary Examiner* — Matthew P Coughlin
*Assistant Examiner* — Ashli Ariana Chicks
(74) *Attorney, Agent, or Firm* — Foley & Lardner LLP; Brittany J. Perla

(57) ABSTRACT

The present disclosure describes processes and intermediates useful for preparing a compound of Formula (Xa) or Formula (Xb). The processes and intermediates can be used to prepare the compounds of the disclosure at multigram or kilogram scale.

(Continued)

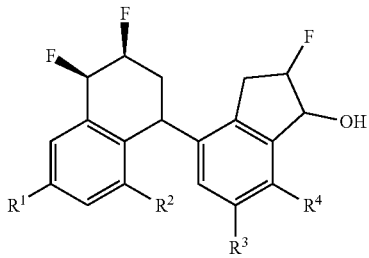

Formula (Xa)

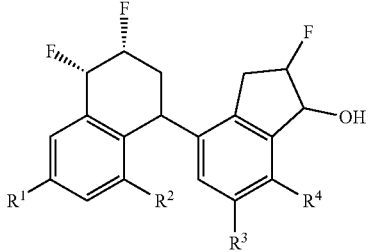

Formula (Xb)

25 Claims, 2 Drawing Sheets

(51) Int. Cl.
 B01J 31/18 (2006.01)
 B01J 31/22 (2006.01)
 C07C 315/04 (2006.01)
 C07C 317/14 (2006.01)
 C07D 317/72 (2006.01)
 C07F 7/12 (2006.01)
 C07F 7/16 (2006.01)
(52) U.S. Cl.
 CPC .......... *C07C 315/04* (2013.01); *C07C 317/14* (2013.01); *C07D 317/72* (2013.01); *C07F 7/12* (2013.01); *C07F 7/16* (2013.01); *B01J 2231/643* (2013.01); *B01J 2531/821* (2013.01); *B01J 2531/824* (2013.01); *C07C 2602/08* (2017.05); *C07C 2602/10* (2017.05)
(58) Field of Classification Search
 CPC ... C07C 317/32; C07C 315/04; C07C 317/14; C07D 317/72; C07F 7/12; C07F 7/16
 See application file for complete search history.

(56) References Cited

U.S. PATENT DOCUMENTS

| 11,787,762 | B2 | 10/2023 | Beatty et al. |
| 2009/0076037 | A1 | 3/2009 | Connoly et al. |
| 2015/0148342 | A1 | 5/2015 | Yue et al. |
| 2019/0233440 | A1 | 8/2019 | Planken et al. |
| 2023/0024438 | A1 | 1/2023 | Beatty et al. |

FOREIGN PATENT DOCUMENTS

| EP | 2 857 393 A1 | 4/2015 |
| FR | 3 071 726 A1 | 4/2019 |
| WO | 2008/107455 A1 | 9/2008 |
| WO | 2014/078479 A2 | 5/2014 |
| WO | 2015/035223 A2 | 3/2015 |
| WO | 2015/095048 A1 | 6/2015 |
| WO | 2016/057242 A1 | 4/2016 |
| WO | 2016/144825 A1 | 9/2016 |
| WO | 2016/144826 A1 | 9/2016 |
| WO | 2016/145032 A1 | 9/2016 |
| WO | 2016/145045 A1 | 9/2016 |
| WO | 2016/145236 A1 | 9/2016 |
| WO | 2016/168510 A1 | 10/2016 |
| WO | 2017/053192 A1 | 3/2017 |
| WO | 2018/031680 A1 | 2/2018 |
| WO | 2019/191227 A1 | 10/2019 |
| WO | 2020/055883 A1 | 3/2020 |
| WO | 2020/081695 A1 | 4/2020 |
| WO | 2020/092100 A1 | 5/2020 |
| WO | 2020/214853 A1 | 10/2020 |
| WO | 2021/016280 A1 | 1/2021 |
| WO | 2021/105069 A1 | 6/2021 |
| WO | 2021/113436 A1 | 6/2021 |

OTHER PUBLICATIONS

Hannedouche et al. J. Am. Chem. Soc. 2004, 126, 986-987 (Year: 2004).*
Daley et al. J. Am. Chem. Soc. 2002, 124, 3680-3691. (Year: 2002).*
Catino, Arthur J. et al., "Benzylic Oxidation Catalyzed by Dirhodium(II,III) Caprolactamate," *Organic Letters* (2005) 7(23):5167-5170.
Clayden, Jonathan et al., "Dearomatizing Cyclization of Arylsulfonylalkoxymethyl Lithiums: A Route to the Podophyllotoxin Skeleton," *Organic Letters* (2003) 5(6):831-834 with Supporting Information (34 pages).
Gopinath, Rangam et al., "Tetrabutylammonium Tribromide (TBATB) as an Efficient Generator of HBr for an Efficient Chemoselective Reagent for Acetalization of Carbonyl Compounds," *J. Org. Chem.* (2002; published on Web Jun. 27, 2002) 67:5842-5845.
Liu, Jack et al., "Effect of acid catalysis on the direct electrophilic fluorination of ketones, ketals, and enamides using Selectfluor," *Tetrahedron Letters* (Mar. 27, 2012) 53:2971-2975.
Nyffeler. Paul T. et al., "Selectfluor: Mechanistic Insight and Applications," *Angew. Chem. Int. Ed.* (2005; published on-line Dec. 1, 2004) 44:192-212.
Ros, Abel et al., "Enantioselective Synthesis of Vicinal Halohydrins via Dynamic Kinetic Resolution," *Organic Letters* (2006) 8(1):127-130.
Touge, Taichiro et al., "Convincing Catalytic Performance of Oxo-Tethered Ruthenium Complexes for Asymmetric Transfer Hydrogenation of Cyclic α-Halogenated Ketones through Dynamic Kinetic Resolution," *Organic Letters* (Mar. 29, 2021) 23:3070-3075.
International Search Report and Written Opinion mailed Apr. 7, 2021 corresponding to PCT/US2020/063000 filed Dec. 3, 2020; 11 pages.
International Search Report and Written Opinion mailed Jun. 23, 2021 corresponding to PCT/US2021/022912 filed Mar. 18, 2021; 19 pages.
Carroll, Veronica A. et al., "Role of Hypoxia-Inducible Factor (HIF)-1α versus HIF-2α in the Regulation of HIF Target Genes in Response to Hypoxia, Insulin-Like Growth Factor-I, or Loss of von Hippel-Lindau Function: Implications for Targeting the HIF Pathway," *Cancer Res* (Jun. 15, 2006) 66(12):6264-6270.
Chen, Wenfang et al., "Targeting Renal Cell Carcinoma with a HIF-2 antagonist," *Nature* (Nov. 3, 2016) 539(7627):112-117.
Cheng, Xiaotong et al, "Marked and rapid effects of pharmacological HIF-2α antagonism on hypoxic ventilatory control," *J. Clin. Invest.* (May 2020; published Mar. 23, 2020) 130(5):2237-2251.
Cho, Hyejin et al., "On-Target Efficacy of a HIF2α Antagonist in Preclinical Kidney Cancer Models," *Nature* (Nov. 3, 2016) 539(7627):107-111.
Cho, Hyejin et al., "Targeting HIF2 in Clear Cell Renal Cell Carcinoma," © 2016 Cho and Kaelin; Published by Cold Spring Harbor Laboratory Press; doi: 10.1101/sqb.2016.81.030833; Cold Spring Harbor Symposia on Quantitative Biology, vol. LXXXI; pp. 113-121.
Choueiri, Toni K. et al., "Targeting the HIF2-VEGF axis in renal cell carcinoma," *Nature Medicine* (published online Oct. 5, 2020); 12 pages.

(56) References Cited

OTHER PUBLICATIONS

Coliat, Pierre et al., "Constitutive or Induced HIF-2 Addiction is Involved in Resistance to Anti-EGFR Treatment and Radiation Therapy in HNSCC," Cancers (Oct. 21, 2019) 11(1607):1-16.
Courtney, Kevin D. et al., "Phase I Dose-Escalation Trial of PT2385, A First-in-Class Hypoxia-Inducible Factor-2α Antagonist in Patients With Previously Treated Advanced Clear Cell Renal Cell Carcinoma," Journal of Clinical Oncology (Mar. 20, 2018) 36(9):867-874.
Dai, Zhiyu et al., "Therapeutic Targeting of Vascular Remodeling and Right Heart Failure in PAH with HIF-2α Inhibitor," American Journal of Respiratory and Critical Care Medicine (Jun. 25, 2018); pp. 1-53.
Ellinghaus, Peter et al., "BAY 87-2243, a highly potent and selective inhibitor of hypoxia-induced gene activation has antitumor activities by inhibition of mitochondrial complex I," Cancer Medicine (2013; accepted Jul. 5, 2013) 2(5):611-624.
Fallah, Jaleh et al., "HIF Inhibitors: Status of Current Clinical Development," Current Oncology Reports (Jan. 22, 2019) 21(6):1-10.
Fieser, Louis F. et al., "Synthesis of 6-Methylaceanthrene 2," Journal of the American Chemical Society (Jan. 1, 1952) 74(2):536-537.
Fuller et al., "Comparison of Desmehylsertraline with Sertraline as a Monoamine Uptake Inhibotor In Vivo," Progress in Neuro-Psychopharmacology & Biological Psychiatry, Prog. Neuoro-Psychopharmacol. & Biol. Psychiat (Jan. 1, 1995) 19(1):135-149.
Gupta, Eva et al., "Targeting HIF-1α and HIF-2α to Overcome Treatment Resistance Mediated by Oncogenic KRAS in Colorectal Cancer," Journal of Cancer Therapy (published online Aug. 2013; accepted Jun. 30, 2013) 4:1132-1139.
Jarman, Edward J. et al., "HER2 regulates HIF-2α and drives an increased hypoxic response in breast cancer," Breast Cancer Research (published online Jan. 22, 2019); 21(10):18 pages.
Kaelin, William G. Jr., M.D., "The VHL Tumor Suppressor Gene: Insights into Oxygen Sensing and Cancer," Transactions of the American Clinical and Climatological Association (2017) vol. 128; 10 pages.
Kizi, Alex et al., "Azepine Product List," In: Chemical catalogue Azepine Ltd, Basingstoke, Hants, XP055811922 (Mar. 1, 2019), 1 page.
Lee, Kyeong et al., "(Aryloxyacetylamino)benzoic Acid Analogues: A New Class of Hypoxia-Inducible Factor-1 Inhibitors," J. Med. Chem. (2007) 50(7):1675-1684.
Li, Jia et al., "Advances in inhibition of protein-protein interactions targeting hypoxia-inducible factor-1 for cancer therapy," Bioorganic & Medicinal Chemistry (Available online Feb. 2, 2019) 27:1145-1158.
Lin, Nan et al., "Hypoxia-inducible factors: key regulators of myeloid cells during inflammation," The Journal of Clinical Investigation (Oct. 2016) 126(10)3661-3671.
Merceron, Christophe et al., "Hypoxia-inducible factor 2α is a negative regulator of osteoblastogenesis and bone mass accrual," Bone Research (Published online Feb. 21, 2019) 7(7): 14 pages.
Metelo, Ana Martins et al., "HIF2a inhibitors for the treatment of VHL disease," Oncotarget (Published Jun. 25, 2015) 6(27):23036-23037.
Miikkulainen, Petra et al., "Hypoxia-inducible factor (HIF)-prolyl hydroxylase 3 (PHD3) maintains high HIF2A mRNA levels in clear cell renal cell carcinoma," J. Biol. Chem. (Published, Jan. 7, 2019) 294(10) 3760-3771.
Murugesan, Thanabal et al., "Targeting HIF-2 as therapy for advanced cancers," Drug Discovery Today (Jul. 2018) 23(7):1444-1451.
Nabi, Shahzaib et al., "Renal cell carcinoma: a review of biology and pathophysiology [version 1; referees: 2 approved]," F1000Research 2018 7(F1000 Faculty Rev):307; (First published Mar. 12, 2018); 10 pages.
Niechi, Ignacio et al., "Adenosine Depletion as a New Strategy to Decrease Glioblastoma Stem-Like Cells Aggressiveness," Cells (Oct. 30, 2019) 8:1353; 15 pages.

Palazon, Asis et al., "HIF Transcription Factors, Inflammation, and Immunity," Immunity (Oct. 16, 2014) 41(4):518-528.
Pechulis, Anthony D. et al., "4-Phenyl tetrahydroisoquinolines as dual norepinephrine and dopamine reuptake inhibitors," Biorganic & Medicinal Chemistry Letters (Sep. 22, 2012) 22(23):7219-7222.
Ricketts, Christopher J. et al., "Targeting HIF2α in Clear-Cell Renal Cell Carcinoma," Cancer Cell (Oct. 10, 2016) 30:515-517.
Rogers, Jamie L. et al., "Development of Inhibitors of the PAS-B Domain of the HIF-2α Transcription Factor," J. Med. Chem. (Jan. 30, 2013) 56:1739-1747.
Sano, H. et al., "Design and synthesis of subtype-selective cyclooxygenase (COX) inhibitors derived from thalidomide," Bioorganic & Medicinal Chemistry (May 2, 2005) 13(9):3079-3091.
Scheuermann, Thomas H. et al., "Allosteric Inhibition of Hypoxia Inducible Factor-2 with Small Molecules," Nat Chem Biol. (Apr. 2013) 9(4):271-276.
Scheuermann, Thomas H. et al., "Isoform-Selective and Stereoselective Inhibition of Hypoxia Inducible Factor-2," J. Med. Chem. (Jul. 30, 2015) 58:5930-5941.
Semenza, Gregg L., "Hypoxia-inducible factors: mediators of cancer progression and targets for cancer therapy," Trends Pharmacol Sci. (Apr. 2012) 33(4):207-214.
Shimoda, Larissa A. et al., "Revisiting the role of hypoxia-inducible factors in pulmonary hypertension," Current Opinion in Physiology (Available online Jan. 7, 2019) 7:33-40.
Thansandote, Praew et al., "Synthesis of Benzannulated N-Heterocycles by a Palladium-Catalyzed C-C/C—N Coupling of Bromoalkylamines," Organic Letters (Dec. 1, 2007) 9(25):5255-5258.
Wallace, Eli M. et al., "A Small-Molecule Antagonist of HIF2α is Efficacious in Preclinical Models of Renal Cell Carcinoma," Cancer Res (Sep. 15, 2016) 76(18):5491-5500.
Wang, Xin et al., "HIF-2α-mediated activation of the epidermal growth factor receptor potentiates head and neck cancer cell migration in response to hypoxia," Carcinogenesis (Apr. 15, 2010) 31(7):1202-1210.
Wehn, Paul M. et al., "Design and Activity of Specific Hypoxia-Inducible Factor-2α (HIF-2α) Inhibitors for the Treatment of Clear Cell Renal Cell Carcinoma: Discovery of Clinical Candidate (s)-3-((2,2-Difluoro-1-hydroxy-7-(methylsulfonyl)-2,3-dihydro-1H-inden-4-yl)oxy)-5-fluorobenzonitrile (PT2385)," J. Med. Chem. (Oct. 5, 2018) 61:9691-9721.
Wu, Dalei et al., "Structural integration in hypoxia-inducible factors," Nature (Aug. 20, 2015) 524:303-308 (17 pages).
Xiang, Lisha et al., "Hypoxia-inducible factors promote breast cancer stem cell specification and maintenance in response to hypoxia or cytotoxic chemotherapy," Advances in Cancer Research; Chapter 5 (© 2019 Elsevier Inc.) ISSN 0065-230X; https://doi.org/10.1016/bs.acr.2018.11.001; 141:175-212.
Yu, Tianchi et al., "Development of Inhibitors Targeting Hypoxia-Inducible Factor 1 and 2 for Cancer Therapy," Yonsei Med J (May 2017; Accepted Nov. 30, 2016) 58(3):489-496.
Zhen, Qiang et al., "Endothelial PAS domain-containing protein 1 confers TKI-resistance by mediating EGFR and MET pathways in non-small cell lung cancer cells," Cancer Biology & Therapy (Apr. 2015; Accepted Feb. 3, 2015) 16(4):549-557.
Gupta, Nupur et al., "Hypoxia-Inducible Factor Prolyl Hydroxylase Inhibitors: A Potential New Treatment for Anemia in Patients with CKD," Am J Kidney Dis. (originally published online Feb. 24, 2017; corrected online Apr. 6, 2017) 69(6):815-826.
International Search Report received from the European Patent Office in related International Application No. PCT/US2021/022912 dated Jun. 9, 2021.
International Preliminary Report on Patentability from the Patent Office in related International Application No. PCT/US2020/06300 dated Jun. 16, 2022.
International Preliminary Report on Patentability received from the International Bureau of WIPO in related International Application No. PCT/US2021/022912 dated Jun. 9, 2021.

\* cited by examiner

PROCESS FOR PREPARING TETRALIN COMPOUNDS

CROSS-REFERENCES TO RELATED APPLICATIONS

This application claims the benefit of priority under 35 U.S.C. § 119(e) to U.S. Provisional Application Ser. No. 63/245,287 filed Sep. 17, 2021, the disclosure of which is incorporated herein by reference in its entirety.

BACKGROUND

Hypoxia-inducible factor (HIF) transcription factors play an integral role in cellular response to low oxygen availability. See, Immunity. 2014 Oct. 16; 41(4): 518-528. HIFs are heterodimeric transcription factors consisting of a common constitutive subunit called the aryl hydrocarbon receptor nuclear translocator (ARNT, or HIF-β) and one of three HIF-α subunits (J. Med. Chem. 2015, 58, 5930-5941.) Under normal conditions, the α-subunits are hydroxylated at conserved proline residues by prolyl-4-hydroxylases (PHDs), and subsequently targeted for degradation by the von Hippel-Lindau (pVHL) ubiquitin E3 ligase complex. See, Cancer Res 2006; 66(12): 6264-70. However, under hypoxic conditions, HIF-α accumulate and enter the nucleus to activate the expression of genes that regulate metabolism, angiogenesis, cell proliferation and survival, immune evasion, and inflammatory response (J. Med. Chem. 2018, 61, 9691-9721.)

Of the three different α-subunit isoforms-HIF-1α, HIF-2α and the less characterized HIF-3α-HIF-1α and HIF-2α overexpression have been associated with poor clinical outcomes in patients with various cancers. Specifically, HIF-2α has been found to be a marker of poor prognosis in glioblastoma, neuroblastoma, head and neck squamous carcinoma, and non-small cell lung cancer. Hypoxia is also prevalent in many acute and chronic inflammatory disorders, such as inflammatory bowel disease and rheumatoid arthritis. See, J. Clin Invest. 2016; 126(10):3661-3671.

Substituted tetralins and their use are described in WO 2021/188769. However, substituted derivatives of this compound pose various synthetic challenges due to the presence of multiple chiral centers in their structures, thereby necessitating complex synthetic protocols when a stereoisomer is desired. As such, there is a need in the art for providing improved processes to prepare substituted tetralin compounds. The present disclosure addresses this need and provides related advantages as well.

BRIEF SUMMARY

Provided herein is a process comprising contacting a compound of Formula (Ia) or (IIb):

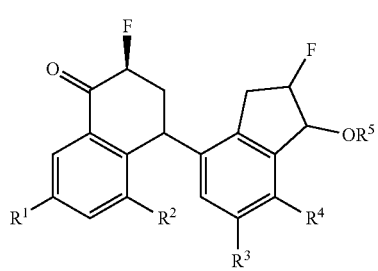

(IIa)

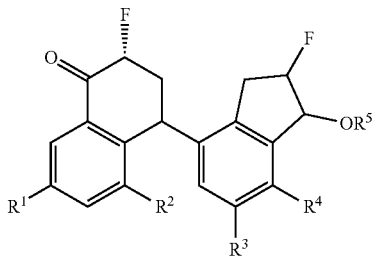

(IIb)

with a chiral ruthenium(II) catalyst and a hydrogen reagent;

thereby preparing a compound of Formula (Ia) or (Ib):

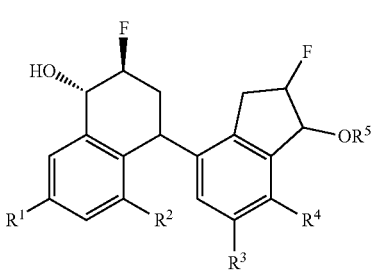

(Ia)

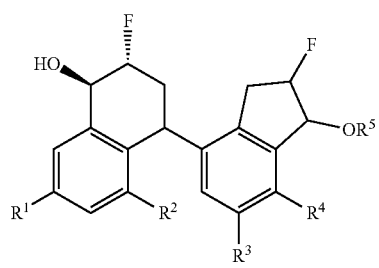

(Ib)

wherein

R$^1$ and R$^2$ are independently selected from —H, —F, —Cl, and —CN;

R$^3$ is —H, —F or —Cl;

R$^4$ is selected from the group consisting of —H, —F, —Cl, —C$_1$-C$_3$ alkyl, and —S(O)$_2$(C$_1$-C$_3$ alkyl), wherein the —C$_1$-C$_3$ alkyl or —S(O)$_2$(C$_1$-C$_3$ alkyl) is optionally substituted with 1-3 halogen;

R$^5$ is an alcohol protecting group; and the compound of Formula (Ia) or (Ib) has at least 90% diastereomeric purity.

Also provided herein is a process of preparing a compound of Formula (Xa) or (Xb):

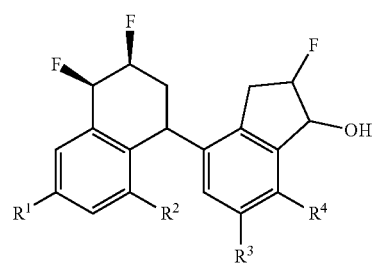

Formula (Xa)

3
-continued

Formula (Xb)

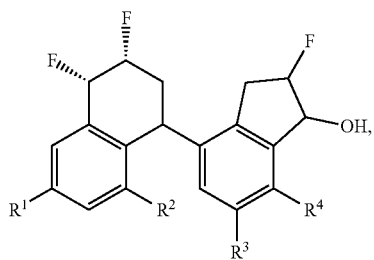

wherein:
R$^1$ and R$^2$ are independently selected from —H, —F, —Cl, and —CN;
R$^3$ is H, F, or Cl; and
R$^4$ is selected from the group consisting of —H, —F, —Cl, —C$_1$-C$_3$ alkyl, and —S(O)$_2$(C$_1$-C$_3$ alkyl), wherein the —C$_1$-C$_3$ alkyl or —S(O)$_2$(C$_1$-C$_3$ alkyl) is optionally substituted with 1-3 halogen;
the process comprising:
(a) contacting a compound of Formula (Ia) or (Ib):

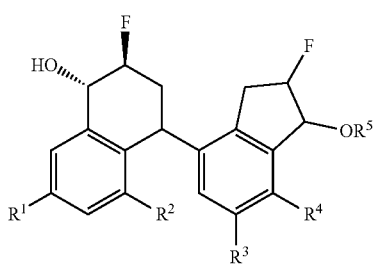

(Ia)

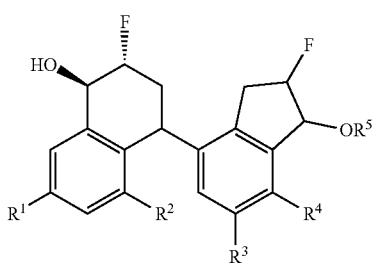

(Ib)

wherein R$^5$ is an alcohol protecting group,
with a fluorinating agent to prepare a compound of Formula (XIa) or (XIb):

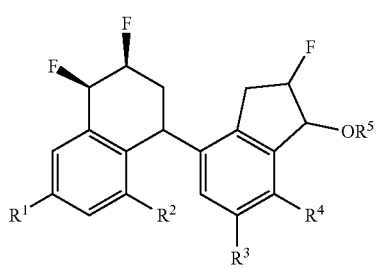

(XIa)

4
-continued

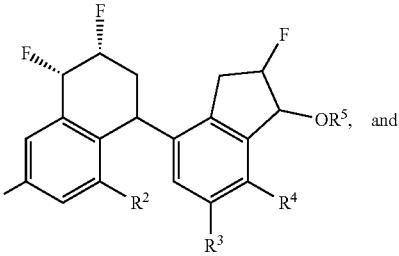

(XIb)

(b) contacting the compound of Formula (XIa) or (XIa) with a deprotecting agent, thereby preparing the compound of Formula (Xa) or (Xb); wherein the compound of Formula (Xa) or (Xb) is prepared in at least a 10 g scale.

DETAILED DESCRIPTION

Figure 1:
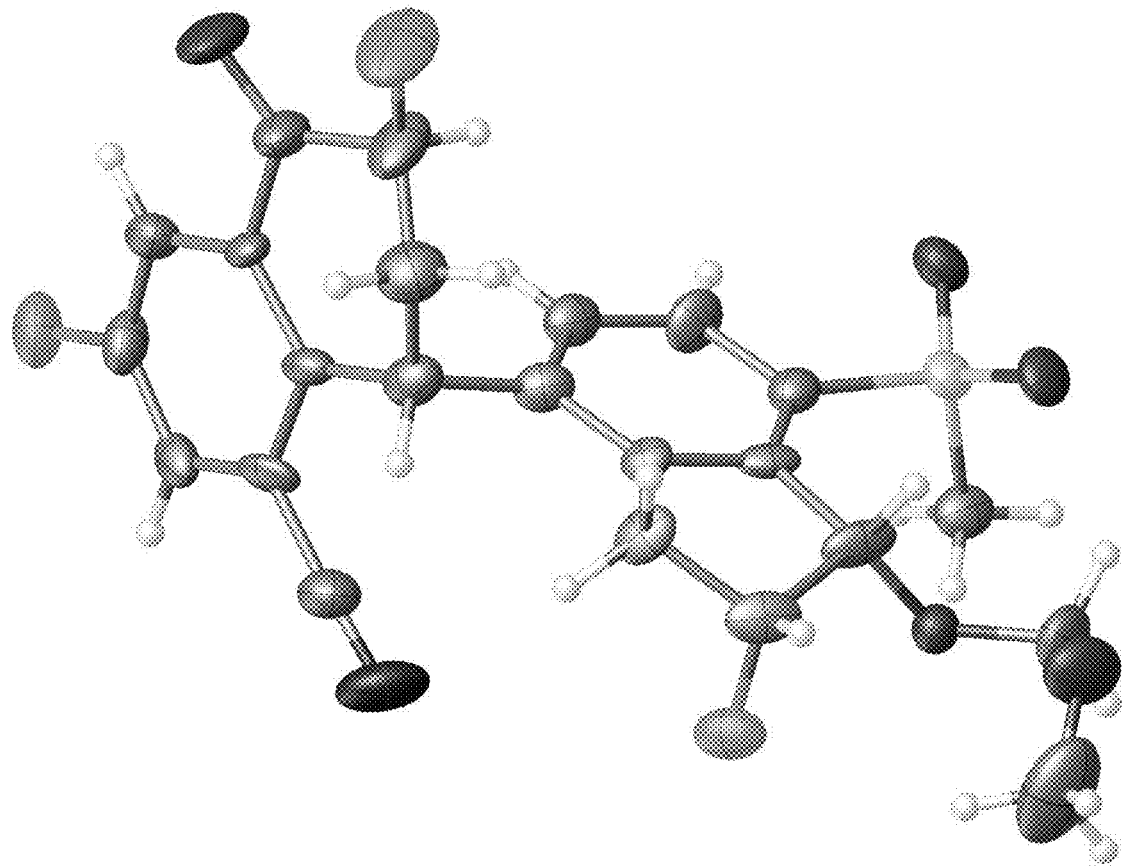
FIG. 1 shows an Oak Ridge Thermal Ellipsoid Plot (ORTEP) diagram of the single crystal x-ray diffraction pattern for Compound 8.

The present disclosure describes stereoselective processes of preparing substituted tetralin compounds. The processes described herein relate to efficient, scalable processes that can be performed at any scale, for example, multigram or kilogram scale.

Definitions

The terms "comprising", "including" and "having" are intended to be inclusive and mean that there may be additional elements other than the listed elements.
"About" when referring to a value includes the stated value +/−10% of the stated value. For example, about 50% includes a range of from 45% to 55%, while about 2.0 molar equivalents includes a range of from 1.8 to 2.2 molar equivalents. Accordingly, when referring to a range, "about" refers to each of the stated values +/−10% of the stated value of each end of the range. For instance, a ratio of from about 1 to about 3 (weight/weight) includes a range of from 0.9 to 3.3.
"Alkyl" is a linear or branched saturated monovalent hydrocarbon. For example, an alkyl group can have 1 to 8 carbon atoms (i.e., —C$_1$-C$_8$ alkyl) or 1 to 6 carbon atoms (i.e., —C$_1$-C$_6$ alkyl) or 1 to 4 carbon atoms (i.e., —C$_1$-C$_4$ alkyl) or 1 to 3 carbon atoms (i.e., —C$_1$-C$_3$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (1-Bu, 1-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2- butyl (—C(CH$_3$)$_2$CH$_2$CH$_3$), 3-methyl-2-butyl (—CH(CH$_3$) CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), and 2,3-dimethyl-2-butyl (—C(CH$_3$)$_2$CH(CH$_3$)$_2$). In some embodiments, the alkyl group is a —C$_1$-C$_3$ alkyl.

"Halo" or "halogen" as used herein refers to fluoro (—F), chloro (—Cl), bromo (—Br) and iodo (—I).

"Purity" refers to chemical purity independent of stereochemistry preference unless otherwise indicated.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers. The methods for the determination of stereochemistry and the separation of stereoisomers are well-known in the art (see, e.g., Chapter 4 of Advanced Organic Chemistry, 4th ed., J. March, John Wiley and Sons, New York, 1992).

The compounds of the embodiments disclosed herein, or their pharmaceutically acceptable salts may contain one or more asymmetric centers and may thus give rise to stereoisomers including, e.g., enantiomers and diastereomers. Stereoisomeric forms may be defined, in terms of absolute stereochemistry, as (R)- or (S)-, and/or depicted using dashes (⋯⋯) and/or wedges (▬▬). The present disclosure is meant to include all such possible isomers, as well as their racemic and optically pure forms. Optically active (+) and (−), or (R)- and (S)-isomers may be prepared using chiral synthons or chiral reagents, or resolved using conventional techniques, for example, chromatography and fractional crystallization. Conventional techniques for the preparation/isolation of individual enantiomers include, for example, chiral synthesis from a suitable optically pure precursor or resolution of the racemate (or the racemate of a salt or derivative) using, for example, chiral high pressure liquid chromatography (HPLC). When a stereochemical depiction (e.g., using dashes, ⋯⋯, and/or wedges, ▬▬) is shown in a chemical structure, it is meant to indicate that the depicted stereoisomer is present and substantially free of one or more other stereoisomer(s) (e.g., enantiomers and/or diastereomers, when present). For example, a compound having an (R) stereocenter can be substantially free of the opposite (S) enantiomer of the compound. An (S, S) compound having two stereocenters can be substantially free of other stereoisomers (e.g., (R, R), (S, R), and (R, S)) of the compound. A compound that is substantially free of other stereoisomers comprises 70% or more, e.g., 75% or more, 80% or more, 85% or more, 90% or more, 95% or more, 97% or more, 98% or more, by weight of one stereoisomer of the compound.

A chemical bond to an asymmetric carbon that is depicted as a solid line (———) indicates that all possible stereoisomers at that carbon atom are included, and may be present as a racemic or scalemic mixture of such compound(s).

As used herein, the term "racemic mixture" refers to a 1:1 mixture of enantiomers.

As used herein, the term "scalemic mixture" refers to a mixture of enantiomers that are at a ratio other than 1:1.

A compound having multiple stereoisomers but only indicating defined stereochemistry for a subset of the stereoisomers is understood to be substantially free of other stereoisomers for the stereocenters indicated. For example, a compound having five stereocenters but only indicating (R, S) stereochemistry for two of the stereocenters is understood to be substantially free of the (R, R), (S, R), and (S, S) isomers for the two indicated stereocenters. However, the compound may have a mixture of stereoisomers at the three undefined stereocenters.

Diastereomeric transformations are those that favor the formation of one diastereoisomer over another. The diastereomeric purity of such transformations is a measure of how selective the transformation is at the stereocenter effected by the transformation.

The present disclosure includes all tautomers of compounds described herein, even if only one tautomer is expressly represented. "Tautomer" refers to alternate forms of a compound that differ in the position of a proton, such as enol-keto tautomers.

"Catalyst" refers to a chemical reactant that increases the rate of a reaction without itself being consumed.

"Protecting group" refers to a moiety of a compound that masks or alters the properties of a functional moiety. The protecting group can be removed so as to restore the functional moiety to its original state. Chemical protecting groups and strategies for protection/deprotection are well known in the art. See also Protective Groups in Organic Chemistry, Peter G. M. Wuts and Theodora W. Greene, 4th Ed., 2006. Protecting groups are often utilized to mask the reactivity of certain functional moieties, to assist in the efficiency of desired chemical reactions, e.g., making and breaking chemical bonds in an ordered and planned fashion. For example, an "alcohol protecting group" refers to a protecting group useful for masking alcohols, e.g., to render alcohols unreactive during intermediate steps of a synthetic process. Exemplary alcohol protecting groups include silyl groups (e.g., trimethylsilyl (TMS), triethylsilyl (TES), tri-isopropylsilyl (TIPS), tert-butyldimethylsilyl (TBS), and tert-butyldiphenylsilyl (TBDPS)), ether groups (e.g., methoxymethyl (MOM), methoxyethoxymethyl (MEM), benzyloxymethyl (BOM), and tetrahydropyranyl (THP)), alkyl groups (e.g., methyl, ethyl, isopropyl, or tert-butyl), trityl groups (e.g., trityl (Tr), 4-monomethoxytrityl (MMTr), and 4,4'-dimethoxytrityl (DMTr)), acyl groups (e.g., acetyl, benzoyl, pivaloyl), tert-butoxycarbanyl (Boc), or benzyl (e.g., benzyl, p-methoxybenzyl (PMB)) groups.

A "protecting agent" is a chemical reactant that is capable of effecting attachment of a protecting group. For example, the protecting agent tert-butyldimethylsilyl chloride may be used to install a tert-butyldimethylsilyl protecting group on an alcohol. A protecting group can subsequently be removed using a deprotecting agent, thereby restoring the functional moiety to its original form.

A "deprotecting agent" is a chemical reactant that is capable of effecting removal of a protecting group. For example, tetra(n-butyl)ammonium fluoride is capable of cleaving a tert-butyldimethylsilyl ether to form an alcohol. The deprotecting agent used will depend on, for example, the identity of the protecting group that is to be removed, and the reactivity of other functional groups present on the molecule. Typical deprotecting agents include reducing agents, oxidizing agents, acids, Lewis acids, bases, fluoride reagents, and enzymes. In general, silyl protecting groups can be removed under acid conditions, or by treatment with a fluoride reagent; ether protecting groups can be removed under acidic conditions; alkyl protecting groups can be removed under reductive conditions, or by treatment with a Lewis acid; trityl protecting groups can be removed under acidic conditions, or by treatment with a Lewis acid; acyl protecting groups can be removed under reductive conditions, under basic conditions, or by treatment with an enzyme; tert-butoxycarbanyl (Boc) protecting groups can be removed under acidic conditions; and benzyl protecting groups can be removed under reductive conditions, or by treatment with a Lewis acid. Exemplary reducing agents include, but are not limited to, hydrogen, metal hydrides (e.g., diisobutylaluminum hydride (DIBAL), and lithium aluminum hydride (LAH)), or borohydrides (e.g., sodium borohydride). Exemplary bases include, but are not limited to, ammonia, methylamine, sodium methoxide, metal hydroxides (e.g., LiOH, NaOH, and KOH), and the like. Exemplary acids include, but are not limited to HCl, formic acid, acetic acid, trifluoroacetic acid, methanesulfonic acid, and the like. Exemplary Lewis acids include, but are not limited to $ZnCl_2$, $ZnBr_2$, $TiCl_4$, $BF_3$, trimethylsilyl iodide (TMSI), and the like. Exemplary oxidizing agents include, but are not limited to dicyanodichloroquinone (DDQ), triethylenediamine (DABCO), poly(4-vinylpyridinium tribromide), hydrogen peroxide, and the like. Exemplary fluoride reagents include, but are not limited to, quaternary ammonium fluoride reagents (e.g., tetra(n-butyl)ammonium fluoride (TBAF), and tris(dimethylamino)sulfur(trimethylsilyl) difluoride (TAS-F)), pyridinium fluoride, potassium fluoride, hydrofluoric acid, and the like. Exemplary enzymes include, but are not limited to, ester hydrolases, or lipases.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). All isotopic variations of the compounds of the present disclosure, whether radioactive or not, are intended to be encompassed within the scope of the present disclosure. In some embodiments, the compounds according to this disclosure are characterized by one or more deuterium atoms.

Compounds

Provided herein are compounds described herein. In some embodiments, the compound is selected from the group consisting of:

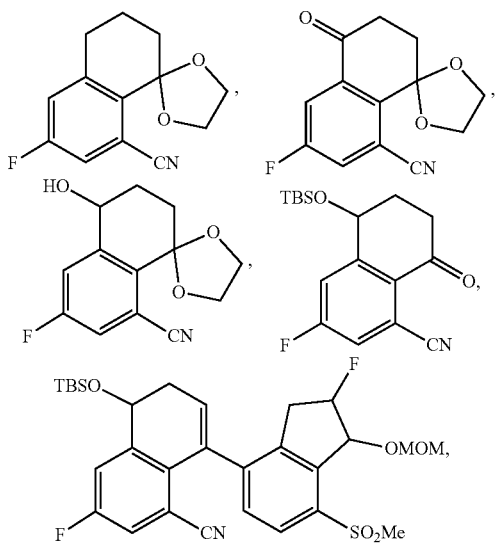

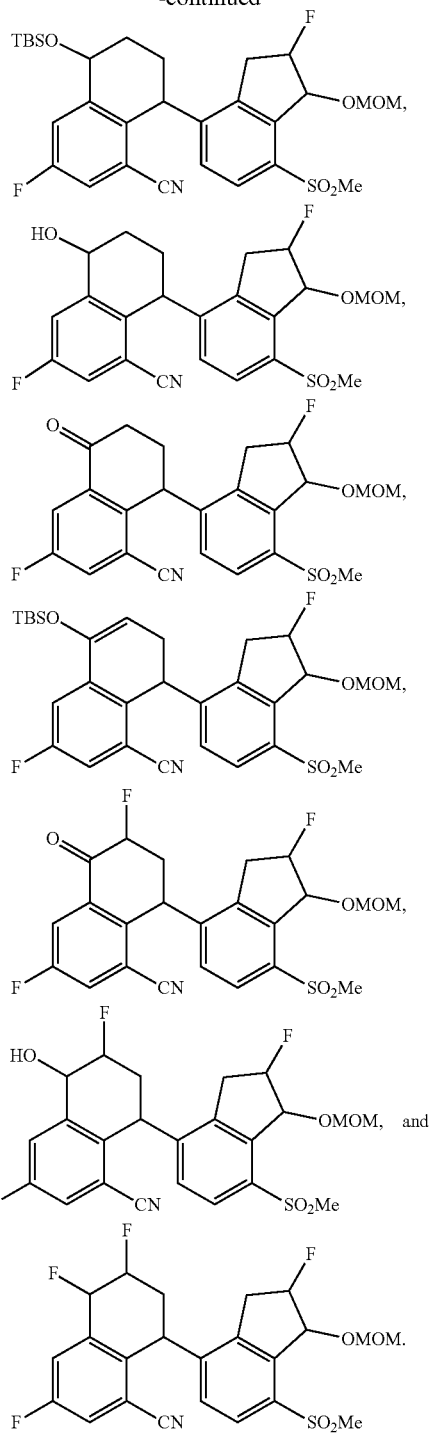

In some embodiments, the compound is selected from:

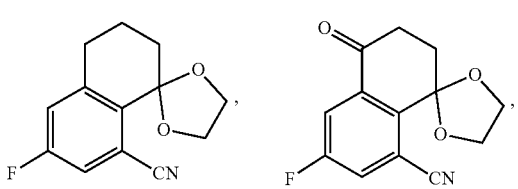

-continued
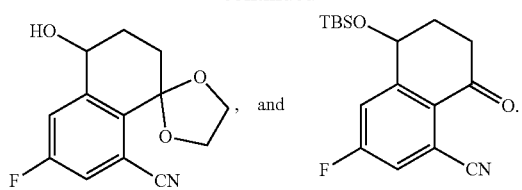
In some embodiments, the compound is selected from:
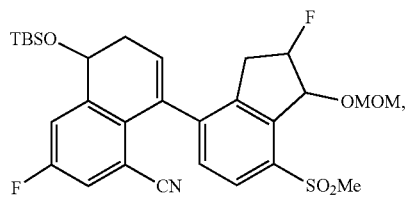
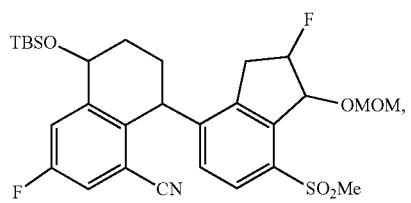
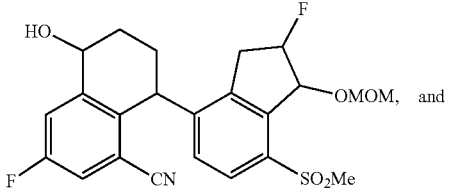
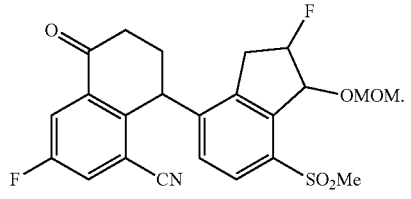
In some embodiments, the compound is selected from:
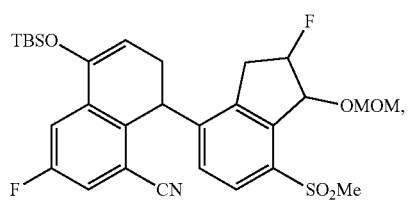
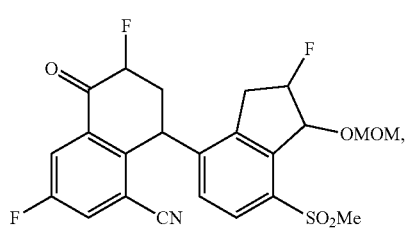
-continued
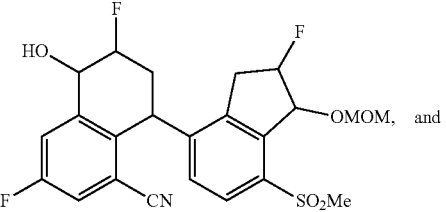
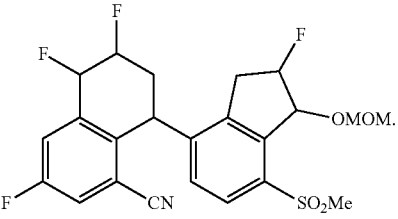
In some embodiments, the compound is selected from the group consisting of:
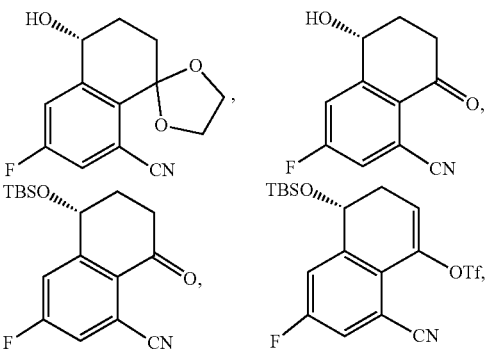
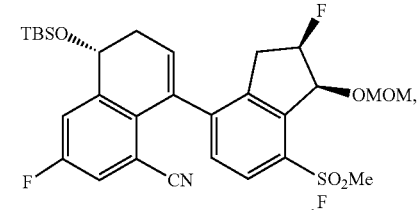
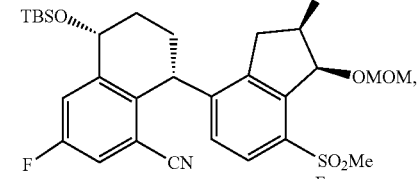
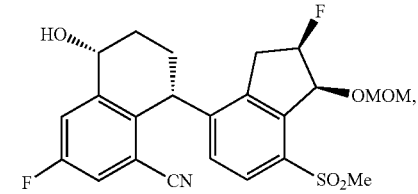
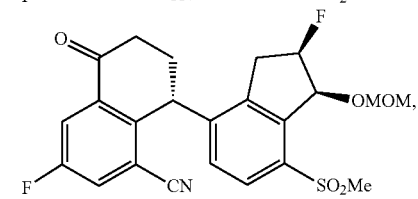

-continued
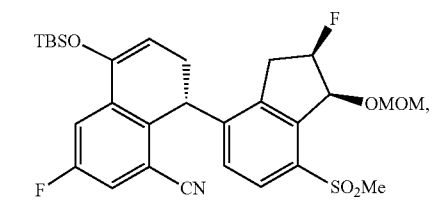
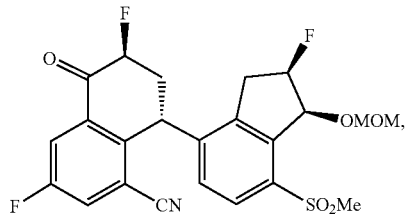
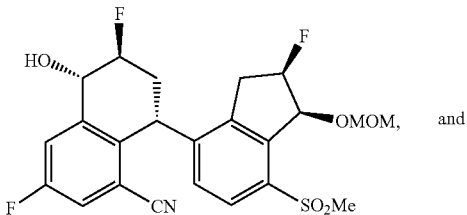
and
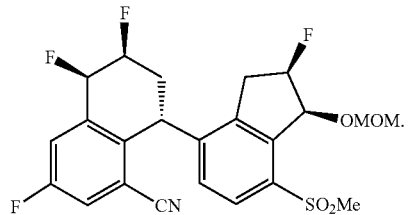
In some embodiments, the compound is selected from:
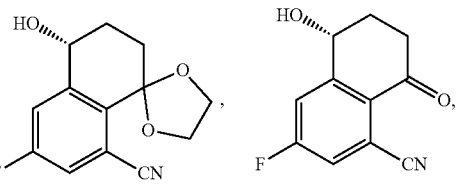
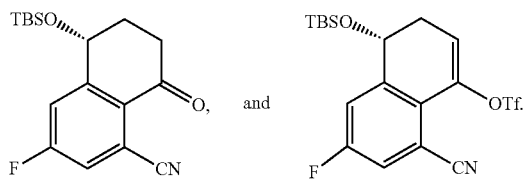
and
In some embodiments, the compound is selected from:
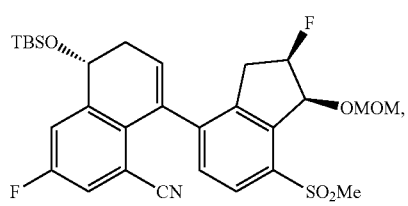
-continued
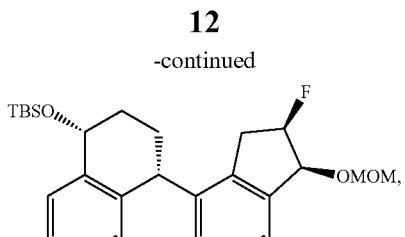
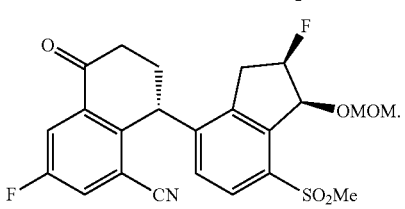
and
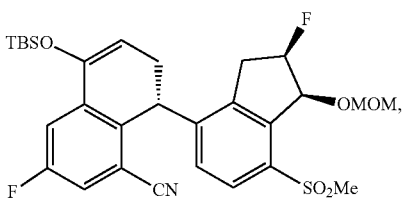
In some embodiments, the compound is selected from:
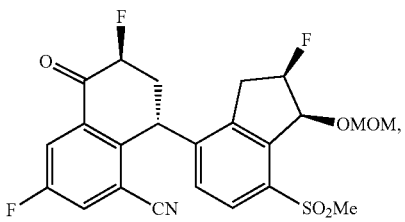
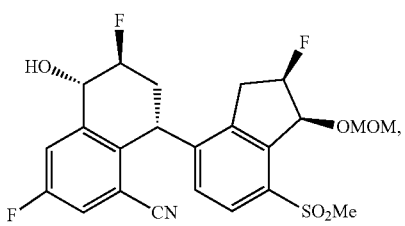
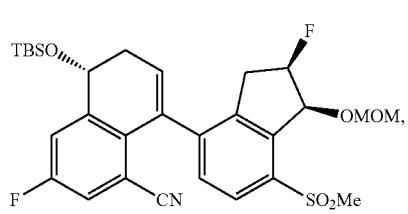
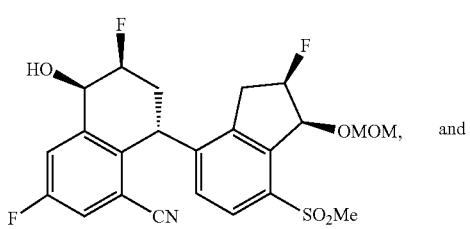
and -continued

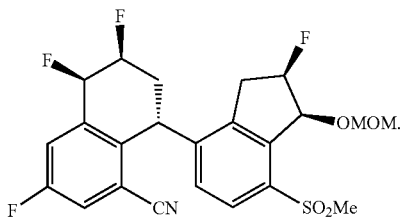

In some embodiments, the compound is:

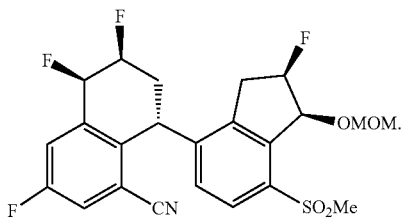

Processes

The present disclosure describes processes to prepare chiral compounds in a stereoselective manner. In some embodiments, the stereoselectivity is achieved through catalyst control. In some embodiments, the stereoselectivity is achieved through substrate control. A process that prepares a compound having multiple stereocenters can achieve the desired stereochemistry through catalyst control, substrate control, or a combination thereof. For example, a process can define one stereoisomer through catalyst control, and then set additional stereoisomers through substrate control.

Provided herein is a process, the process comprising contacting a compound of Formula (IIa) or (IIb):

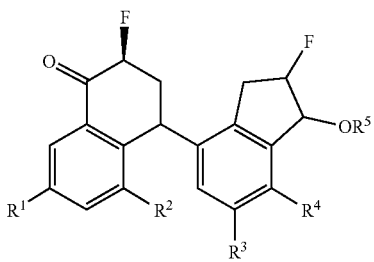

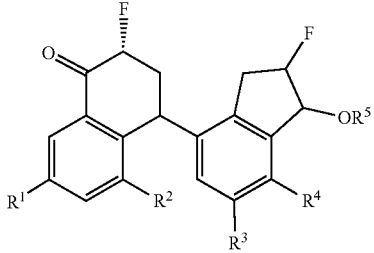

with a chiral ruthenium(II) catalyst and a hydrogen reagent;

thereby preparing a compound of Formula (Ia) or (Ib):

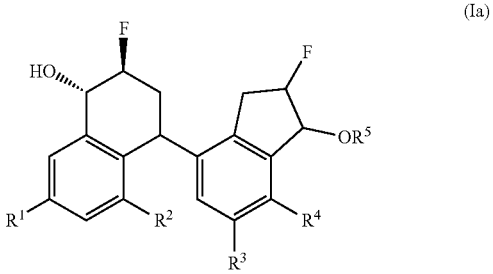

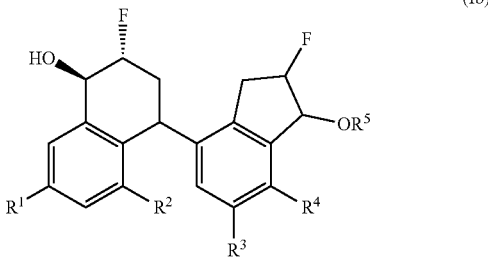

wherein $R^1$ and $R^2$ are independently selected from —H, —F, —Cl, and —CN;

$R^3$ is —H, —F or —Cl;

$R^4$ is selected from the group consisting of —H, —F, —Cl, —$C_1$-$C_3$ alkyl, and —S(O)$_2$($C_1$-$C_3$ alkyl), wherein the —$C_1$-$C_3$ alkyl or —S(O)$_2$($C_1$-$C_3$ alkyl) is optionally substituted with 1-3 halogen;

$R^5$ is an alcohol protecting group; and the compound of Formula (Ia) or (Ib) has at least 90% diastereomeric purity.

In some embodiments, the compound of Formula (Ia) or (Ib) has at least 91%, such as at least 92%, 93%, 94%, 95%, 96%, 97%, 98%, 99%, or at least 99.5% diastereomeric purity.

In some embodiments, the stereochemical outcome from the conversion of the compound of Formula (IIa) or (IIb) to the compound of Formula (Ia) or (Ib) is catalyst controlled.

Suitable chiral ruthenium(II) catalysts include but are not limited to RuCl[(S,S)-Fsdpen](p-cymene), RuCl[(R,R)-Fsdpen](p-cymene), RuCl[(S,S)-Ts-DPEN](p-cymene), RuCl[(R,R)-Ts-DPEN](p-cymene), RuCl[(S,S)-Ts-DPEN](mesitylene), RuCl[(R,R)-Ts-DPEN](mesitylene), chloro[(S,S)—N-[2-(4-methylbenzyloxy)ethyl]-N'-(p-toluenesulfonyl)-1,2-diphenylethylenediamine]ruthenium(II) ((S,S)-Ts-DENEB®), chloro[(S,S)—N-[2-(4-methylbenzyloxy)ethyl]-N'-(p-toluenesulfonyl)-1,2-diphenylethylenediamine]ruthenium(II) ((R,R)-Ts-DENEB®), RuCl$_2$[(S)-dm-Segphos®][(S)-daipen], RuCl$_2$[(R)-dm-Segphos®][(R)-daipen], RuCl$_2$[(S)-dm-Segphos®][(S,S)-dpen], RuCl$_2$[(R)-dm-Segphos®][(R,R)-dpen], RuCl$_2$[(S)-xylbinap][(S)-daipen], RuCl$_2$[(R)-xylbinap][(R)-diapen], RuCl$_2$[(S)-xylbinap][(S)-dpen], RuCl$_2$[(R)-xylbinap][(R)-dpen], RuCl[(S)-daipena][(S)-xylbinap], and RuCl[(R)-daipena][(R)-xylbinap]. In some embodiments, the chiral ruthenium(II) catalyst has the formula:

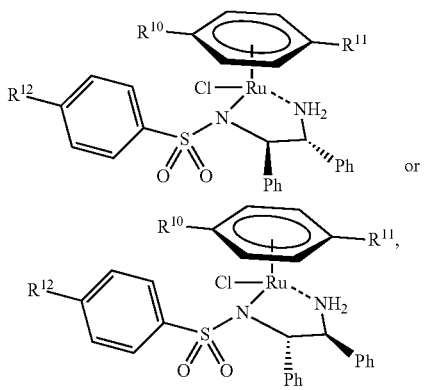

wherein $R^{10}$, $R^{11}$, and $R^{12}$ are each independently —$C_1$-$C_6$ alkyl. In some embodiments, the chiral ruthenium(II) catalyst is RuCl(p-cymene)[(R,R)-Ts-DPEN] or RuCl(p-cymene)[(S,S)-Ts-DPEN].

In some embodiments, the hydrogen reagent is hydrogen gas or formic acid. For example, the hydrogen reagent can be formic acid.

In some embodiments, the process comprises contacting a compound of Formula (IIa) with RuCl(p-cymene)[(R,R)-Ts-DPEN] and formic acid, thereby preparing a compound of Formula (Ia).

In some embodiments, the process comprises contacting a compound of Formula (IIb) with RuCl(p-cymene)[(S,S)-Ts-DPEN] and formic acid, thereby preparing a compound of Formula (Ib).

In some embodiments of the processes of the disclosure, the compound of Formula (Ia) is a compound of Formula (Ia-1), (Ia-2), and/or (Ia-3):

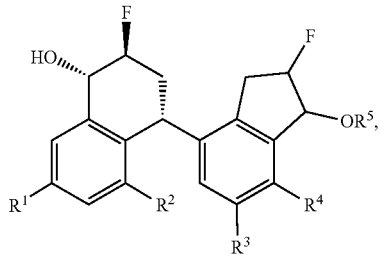

(Ia-1)

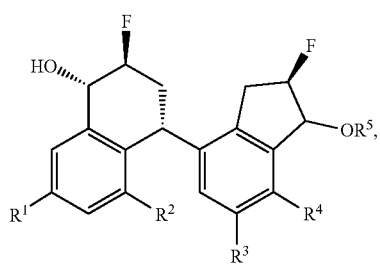

(Ia-2)

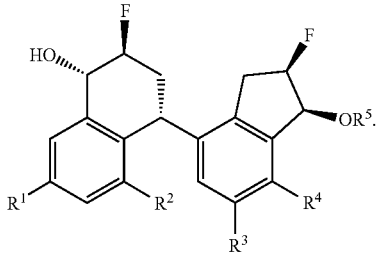

(Ia-3)

In some embodiments, the compound of Formula (Ia), (Ia-1), (Ia-2), and/or (Ia-3) is substantially free of other stereoisomers. In some embodiments, the compound of Formula (Ia) is a compound of Formula (Ia-3) that is substantially free of other stereoisomers.

In some embodiments of the processes of the disclosure, the compound of Formula (Ib) is a compound of Formula (Ib-1), (Ib-2), and/or (Ib-3):

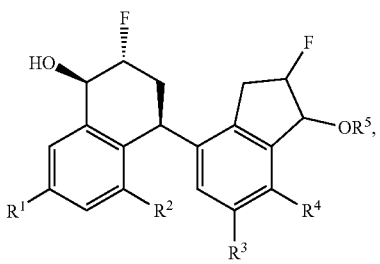

(Ib-1)

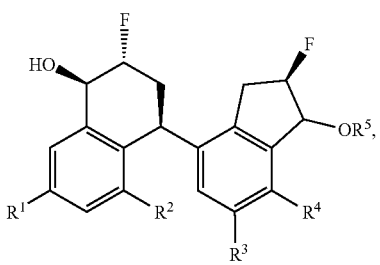

(Ib-2)

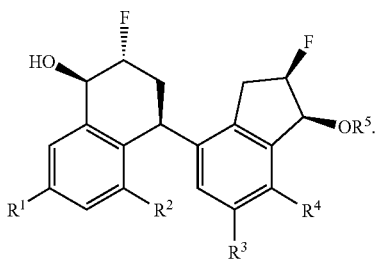

(Ib-3)

In some embodiments, the compound of Formula (Ib), (Ib-1), (Ib-2), and/or (Ib-3) is substantially free of other stereoisomers. In some embodiments, the compound of Formula (Ib) is a compound of Formula (Ib-3) that is substantially free of other stereoisomers.

In some embodiments of the processes of the disclosure, the compound of Formula (IIa) is a compound of Formula (IIa-1), (IIa-2), and/or (IIa-3):

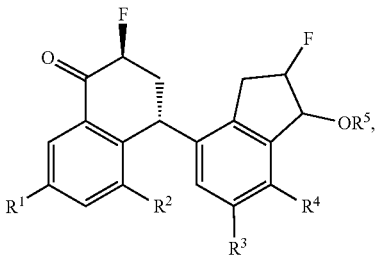
(IIa-1)

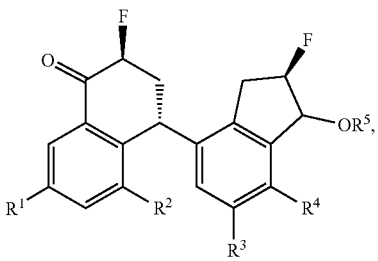
(IIa-2)

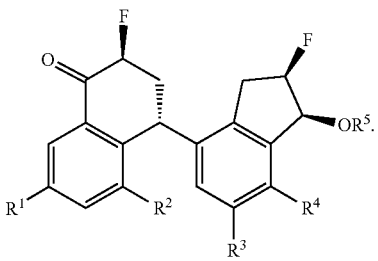
(IIa-3)

In some embodiments, the compound of Formula (IIa), (IIa-1), (IIa-2), and/or (IIa-3) is substantially free of other stereoisomers. In some embodiments, the compound of Formula (IIa) is a compound of Formula (IIa-3) that is substantially free of other stereoisomers.

In some embodiments of the processes of the disclosure, the compound of Formula (IIb) is a compound of Formula (IIb-1), (IIb-2), and/or (IIb-3):

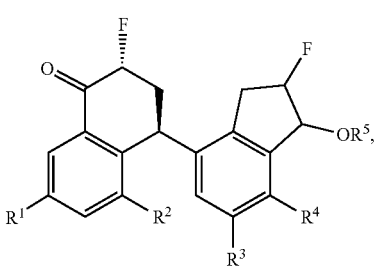
(IIb-1)

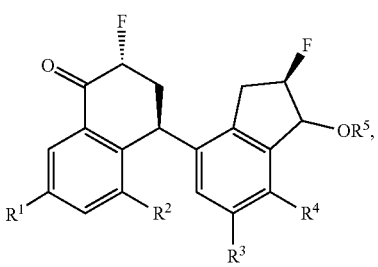
(IIb-2)

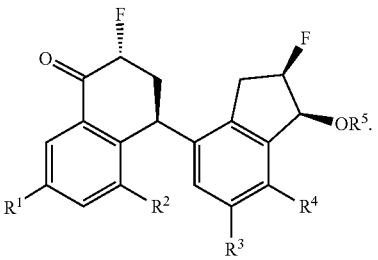
(IIb-3)

In some embodiments, the compound of Formula (IIb), (IIb-1), (IIb-2), and/or (IIb-3) is substantially free of other stereoisomers. In some embodiments, the compound of Formula (IIb) is a compound of Formula (IIb-3) that is substantially free of other stereoisomers.

Any suitable solvent can be used in preparing the compound of Formula (Ia) or (Ib) in the processes described herein. Exemplary solvents include nitriles (e.g., acetonitrile, butyronitrile, etc.), esters (e.g., ethyl acetate, isobutyl acetate, butyl acetate, etc), ethers (diethyl ether, methyl tert-butyl ether, tetrahydrofuran, 2-methyltetrahydrofuran, 1,4-dioxane, cyclopentyl methyl ether, etc.), aromatic hydrocarbons (e.g., toluene, benzene, xylenes, etc.), polar aprotic solvents (e.g., dimethyl sulfoxide, dimethylformamide, etc.), polar protic solvents (e.g., water, ethanol, methanol, formic acid, etc.), chlorinated solvents (e.g., chloroform, dichloromethane, dichloroethane, etc.), or any combinations thereof. In some embodiments, the process further comprises a solvent that is an ether solvent or a chlorinated solvent. In some embodiments, the process further comprises a solvent that is tetrahydrofuran (THF), 2-methyltetrahydrofuran, diethyl ether, methyl tert-butyl ether, cyclopentyl methyl ether, formic acid, benzene, toluene, 1,2-dichloroethane, dichloromethane, chloroform, or chlorobenzene, or any combinations thereof. In some embodiments, the process further comprises a solvent that is dichloromethane. In some embodiments, the process further comprises a solvent that is a formic acid/$Et_3N$ mixture.

Any suitable temperature can be used in preparing the compound of Formula (Ia) or (Ib). In some embodiments, the process further comprises a temperature of from about −78° C. to about 40° C. In some embodiments, the process further comprises a temperature of from about −20° C. to about 25° C. In some embodiments, the process further comprises a temperature of from about −10° C. to about 10° C. In some embodiments, the process further comprises a temperature of from about 0° C. to about 10° C. In some embodiments, the process further comprises a temperature of about 4° C.

The processes of the present disclosure can provide the compound of Formula (Ia) or (Ib) from the compound of Formula (IIa) or (IIb) in a yield of at least 50%, 55%, 60%, 65%, 70%, 75%, 80%, 85%, 90%, 95%, 97%, 98%, or at least 99%. In some embodiments, the yield of the compound of Formula (Ia) or Formula (Ib) is from about 60% to about 100%. In some embodiments, the yield of the compound of Formula (Ia) or Formula (Ib) is from about 70% to about 80% or from about 75% to about 85%. In some embodiments, the yield of the compound of Formula (Ia) or Formula (Ib) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (Ia) or Formula (Ib) is from about 60% to about 90%. In some embodiments, the yield of the compound of Formula (Ia) or Formula (Ib) is from about 70% to about 90%. In some embodiments, the yield of the compound of Formula (Ia) or Formula (Ib) is from about 70% to about 80%.

The processes of the present disclosure can provide the compound of Formula (Ia) or (Ib) from the compound of Formula (IIa) or (IIb) in a purity of from about 80% to about 100%, such as from about 85% to about 100%, from about 90% to about 100%, from about 95% to about 100%, or from about 98% to about 100%.

In some embodiments, the process further comprises preparing the compound of Formula (IIa) or (IIb), the process comprising contacting a compound of Formula (III):

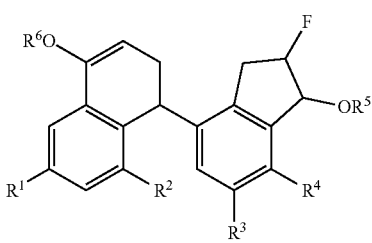

(III)

with an electrophilic fluorinating agent, wherein $R^6$ is an alcohol protecting group, thereby preparing the compound of Formula (IIa) or (IIb).

In some embodiments, the stereochemical outcome from the conversion of the compound of Formula (III) to the compound of Formula (IIa) or (IIb) is substrate controlled.

Any suitable electrophilic fluorinating agent known in the art can be used in the processes described herein. See, Ni, C. et al. *Chem. Rev.* 2015, 115, 2, 765-825; and Umemoto, T et al. *Beilstein J. Org. Chem.* 2021, 17, 1752-1813. Suitable electrophilic fluorinating agents include, but are not limited to, 1-chloromethyl-4-fluoro-1,4-diazoniabicyclo[2.2.2]octane bis(tetrafluoroborate) (Selecfluor®), N-fluoro-N'-methyl-triethylenediamine bis(tetrafluoroborate) (Selectfluor® II), N-fluorobenzenesulfonamide (NFSI), 1,1'-difluoro-2,2'-bipyridinium bis(tetrafluoroborate) (Synfluor), 1-fluoropyridinium trifluoromethanesulfonate, and N-fluoropyridinium (NFPy) salts including, e.g., 1-fluoro-2,4,6-trimethylpyridinium tetrafluoroborate, 1-fluoro-2,3,4,5,6-pentachloropyridinium tetrafluoroborate, and 1-fluoro-2,6-dichloropyridinium tetrafluoroborate. In some embodiments, the electrophilic fluorinating agent is N-fluoro-o-benzenedisulfonimide (NFOBS), N-fluorobenzenesulfonimide (NFSI), or 1-chloromethyl-4-fluoro-1,4-diazoniabicyclo[2.2.2]octane bis(tetrafluoroborate). In some embodiments, the electrophilic fluorinating agent is 1-chloromethyl-4-fluoro-1,4-diazoniabicyclo[2.2.2]octane bis(tetrafluoroborate).

In some embodiments of the processes of the disclosure, the compound of Formula (III) is a compound of Formula (III-1), (III-2), and/or (III-3):

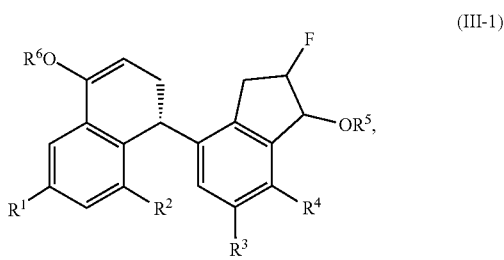

(III-1)

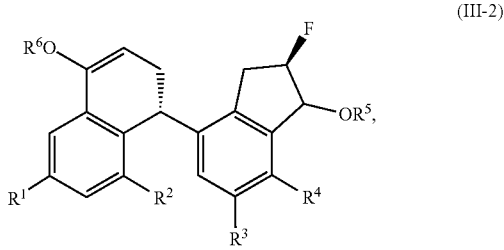

(III-2)

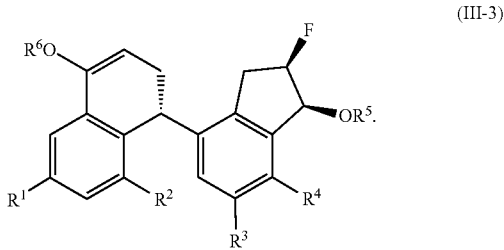

(III-3)

In some embodiments, the compound of Formula (III), (III-1), (III-2), and/or (III-3) is substantially free of other stereoisomers. In some embodiments, the compound of Formula (III) is a compound of Formula (III-3) that is substantially free of other stereoisomers.

In some embodiments of the processes of the disclosure, the compound of Formula (III) is a compound of Formula (III-4), (III-5), and/or (III-6):

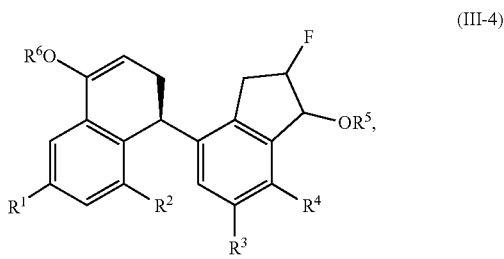

(III-4)

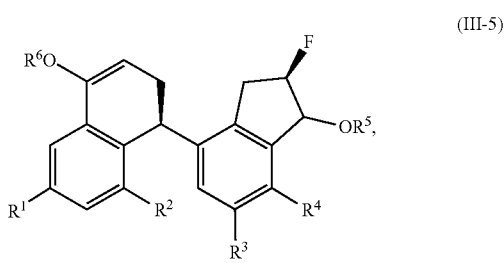

(III-5)

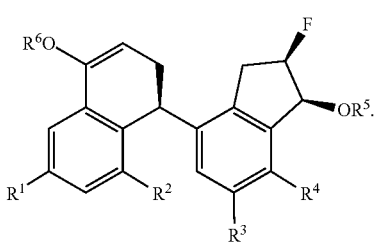

(III-6)

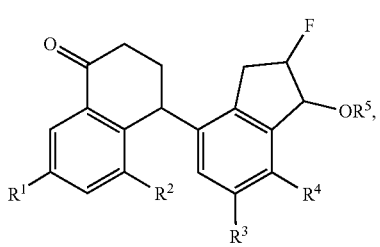

(IV)

In some embodiments, the compound of Formula (III-4), (III-5), and/or (III-6) is substantially free of other stereoisomers. In some embodiments, the compound of Formula (III) is a compound of Formula (III-6) that is substantially free of other stereoisomers.

In some embodiments, $R^6$ is a silyl protecting group, such as a trialkylsilyl or a triarylsilyl protecting group. In some embodiments, $R^6$ is trimethylsilyl (TMS), triethylsilyl (TES), triisopropylsilyl (TIPS), triphenylsilyl (TPS), or tert-butyldimethylsilyl (TBS). In some embodiments, $R^6$ is tert-butyldimethylsilyl (TBS).

Any suitable solvent can be used in preparing the compound of Formula (IIa) or (IIb) in the processes described herein. Exemplary solvents include nitriles (e.g., acetonitrile, butyronitrile, etc.), esters (e.g., ethyl acetate, isobutyl acetate, butyl acetate, etc), ethers (diethyl ether, methyl tert-butyl ether, tetrahydrofuran, 2-methyltetrahydrofuran, 1,4-dioxane, etc.), aromatic hydrocarbons (e.g., toluene, benzene, xylenes, etc.), polar aprotic solvents (e.g., dimethyl sulfoxide, dimethylformamide, etc.), chlorinated solvents (e.g., chloroform, dichloromethane, dichloroethane, etc.), or any combinations thereof. In some embodiments, the process further comprises a solvent that is acetonitrile, tetrahydrofuran (THF), 2-methyltetrahydrofuran, diethyl ether, methyl tert-butyl ether, cyclopentyl methyl ether, toluene, benzene, n-heptane, 1,2-dichloroethane, dichloromethane, chloroform, or chlorobenzene, or a combination thereof. In some embodiments, the process further comprises a solvent that is acetonitrile, tetrahydrofuran (THF), 2-methyltetrahydrofuran, diethyl ether, methyl tert-butyl ether, 1,2-dichloroethane, dichloromethane, chloroform, or chlorobenzene. In some embodiments, the process further comprises a solvent that is acetonitrile, diethyl ether, tetrahydrofuran, dichloromethane, or chloroform. In some embodiments, the process further comprises a solvent that is acetonitrile.

Any suitable temperature can be used in preparing the compound of Formula (IIa) or (IIb). In some embodiments, the process further comprises a temperature of from about −78° C. to about 60° C. In some embodiments, the process further comprises a temperature of from about −20° C. to about 50° C. In some embodiments, the process further comprises a temperature of from about 0° C. to about 50° C. In some embodiments, the process further comprises a temperature of from about 20° C. to about 40° C.

In some embodiments of the process, the process comprises contacting a compound of Formula (IV):

with a $R^6X$ reagent and a base, wherein
$R^6$ is an alcohol protecting group,
X is —Cl, —Br, —I, -OMs, -OTs, or -OTf, and
the base is an amine, an amide, a carbonate, a phosphate, a tetra alkyl ammonium salt, or a hydroxide salt, thereby preparing a compound of Formula (III).

In some embodiments the base is an amine (e.g., triethylamine, diisopropylethylamine, ethyldiisopropylamine, etc.), an amide (e.g., LDA, LiHMDS, NaHMDS, or KHMDS), a carbonate (e.g., cesium carbonate, potassium carbonate, sodium carbonate, etc.), a phosphate (e.g., potassium phosphate, etc.), a tetra alkyl ammonium salt (e.g., tetrabutyl ammonium fluoride), or a hydroxide salt (e.g., NaOH, KOH, etc.). In some embodiments, the base is triethylamine.

Any suitable solvent can be used in preparing the compound of Formula (III) in the processes described herein. Exemplary solvents include nitriles (e.g., acetonitrile, butyronitrile, etc.), ethers (diethyl ether, methyl tert-butyl ether, tetrahydrofuran, 2-methyltetrahydrofuran, 1,4-dioxane, etc.), aromatic hydrocarbons (e.g., toluene, benzene, xylenes, etc.), polar aprotic solvents (e.g., dimethyl sulfoxide, dimethylformamide, etc.), chlorinated solvents (e.g., chloroform, dichloromethane, dichloroethane, etc.), or any combinations thereof. In some embodiments, the process further comprises a solvent that is an ether solvent or a chlorinated solvent. In some embodiments, the process further comprises a solvent that is tetrahydrofuran (THF), 2-methyltetrahydrofuran, diethyl ether, methyl tert-butyl ether, cyclopentyl methyl ether, toluene, benzene, n-heptane, 1,2-dichloroethane, dichloromethane, chloroform, or chlorobenzene, or a combination thereof. In some embodiments, the process further comprises a solvent that is dichloromethane.

Any suitable temperature can be used in preparing the compound of Formula (III). In some embodiments, the process further comprises a temperature of from about −78° C. to about 60° C. In some embodiments, the process further comprises a temperature of from about −20° C. to about 50° C. In some embodiments, the process further comprises a temperature of from about 0° C. to about 50° C. In some embodiments, the process further comprises a temperature of from about 0° C. to about 25° C.

In some embodiments, the process comprises contacting a compound of Formula (IV) with an electrophilic fluorinating agent, thereby preparing a compound of Formula (IIa) or (IIb).

In some embodiments of the processes of the disclosure, the compound of Formula (IV) is a compound of Formula (IV-1), (IV-2), and/or (IV-3):

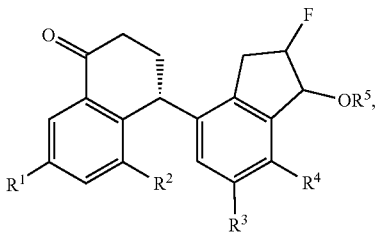

(IV-1)

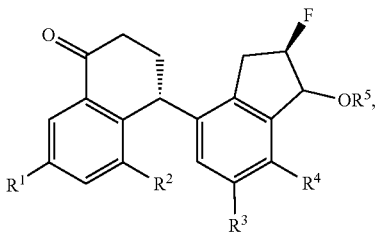

(IV-2)

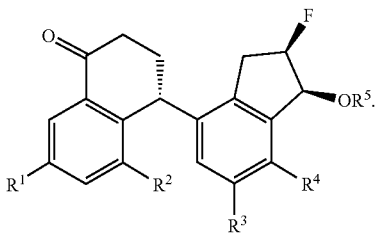

(IV-3)

In some embodiments, the compound of Formula (IV), (IV-1), (IV-2), and/or (IV-3) is substantially free of other stereoisomers. In some embodiments, the compound of Formula (IV) is a compound of Formula (IV-3) that is substantially free of other stereoisomers.

In some embodiments of the processes of the disclosure, the compound of Formula (IV) is a compound of Formula (IV-4), (IV-5), and/or (IV-6):

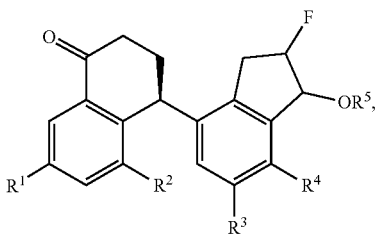

(IV-4)

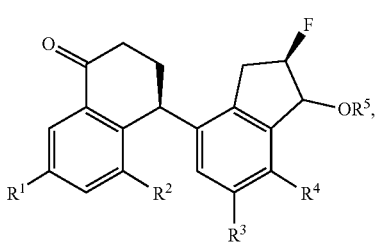

(IV-5)

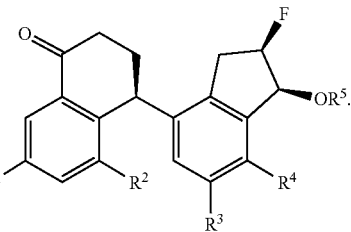

(IV-6)

In some embodiments, the compound of Formula (IV-4), (IV-5), and/or (IV-6) is substantially free of other stereoisomers. In some embodiments, the compound of Formula (IV) is a compound of Formula (IV-6) that is substantially free of other stereoisomers.

In some embodiments, the process comprises preparing the compound of Formula (IV), the process comprising contacting a compound of Formula (V):

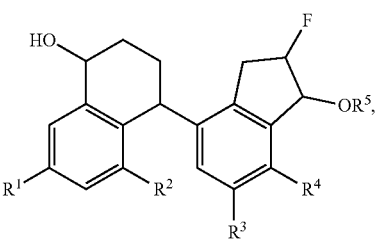

(V)

with an oxidizing agent, thereby preparing the compound of Formula (IV).

Any suitable oxidizing agent known in art can be used in preparing the compound of Formula (IV). In some embodiments, the oxidizing agent is selected from potassium permanganate, a hypervalent iodine compound (e.g., 1,1,1-tris(acetyloxy)-1,1-dihydro-1,2-benziodoxol-3-(1H)-one (Dess-Martin periodinane, DMP), 2-iodoxybenzoic acid (IBX), 1-acetoxy-5-bromo-1,2-benziodoxol-3(1H)-one (ABBX)), oxalyl chloride-dimethyl sulfoxide (DMSO), tert-butyl hydroperoxide, sodium hypochlorite, and chromium (VI) trioxide. In some embodiments, the oxidizing agent is 1,1,1-tris(acetyloxy)-1,1-dihydro-1,2-benziodoxol-3-(1H)-one.

Any suitable solvent can be used in preparing the compound of Formula (IV) in the processes described herein. Exemplary solvents include nitriles (e.g., acetonitrile, butyronitrile, etc.), esters (e.g., ethyl acetate, isobutyl acetate, butyl acetate, etc), ethers (diethyl ether, methyl tert-butyl ether, tetrahydrofuran, 2-methyltetrahydrofuran, 1,4-dioxane, etc.), aromatic hydrocarbons (e.g., toluene, benzene, xylenes, etc.), aliphatic hydrocarbons (e.g., pentane, hexane, etc.), chlorinated solvents (e.g., chloroform, dichloromethane, dichloroethane, etc.), or any combinations thereof. In some embodiments, the process further comprises a solvent that is an ether solvent or a chlorinated solvent. In some embodiments, the process further comprises a solvent that is tetrahydrofuran (THF), 2-methyltetrahydrofuran, methyl tert-butyl ether, cyclopentyl methyl ether, toluene, n-heptane, 1,2-dichloroethane, dichloromethane, chloroform, or chlorobenzene, or a combination thereof. In some embodiments, the process further comprises a solvent that is diethyl ether, methyl tert-butyl ether, tetrahydrofuran, 2-methyltetrahydrofuran, 1,4-dioxane, chloroform, dichloromethane, or dichloroethane. In some embodiments, the process further comprises a solvent that is dichloromethane.

Any suitable temperature can be used in preparing the compound of Formula (IV). In some embodiments, the process further comprises a temperature of from about −78° C. to about 60° C. In some embodiments, the process further comprises a temperature of from about −20° C. to about 50° C. In some embodiments, the process further comprises a temperature of from about 0° C. to about 50° C. In some embodiments, the process further comprises a temperature of from about −10° C. to about 10° C. In some embodiments, the process further comprises a temperature of about 0° C.

In some embodiments of the processes of the disclosure, the compound of Formula (V) is a compound of Formula (V-1), (V-2), and/or (V-3):

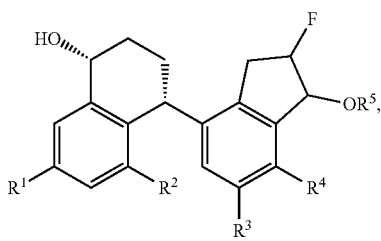
(V-1)

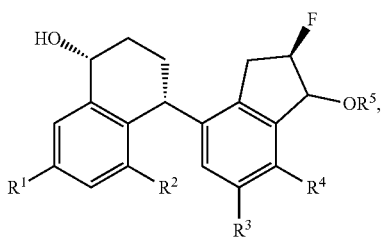
(V-2)

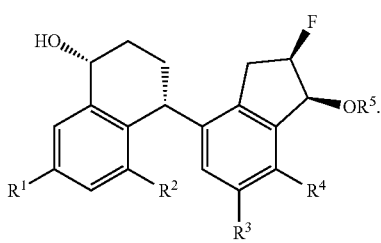
(V-3)

In some embodiments, the compound of Formula (V), (V-1), (V-2), and/or (V-3) is substantially free of other stereoisomers. In some embodiments, the compound of Formula (V) is a compound of Formula (V-3) that is substantially free of other stereoisomers.

In some embodiments of the processes of the disclosure, the compound of Formula (V) is a compound of Formula (V-4), (V-5), and/or (V-6):

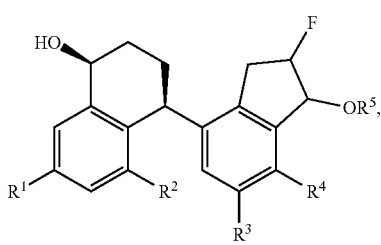
(V-4)

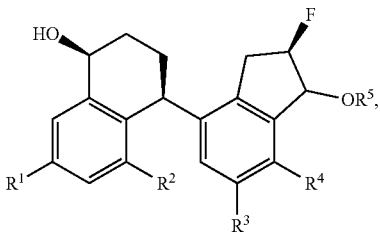
(V-5)

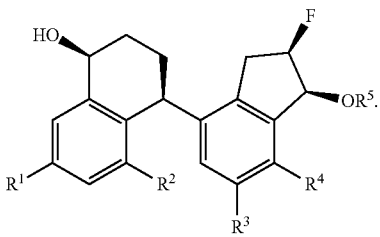
(V-6)

In some embodiments, the compound of Formula (V-4), (V-5), and/or (V-6) is substantially free of other stereoisomers. In some embodiments, the compound of Formula (V) is a compound of Formula (V-6) that is substantially free of other stereoisomers.

In some embodiments, the process comprises: (a) contacting a compound of Formula (VI):

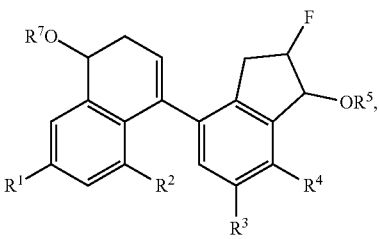
(VI)

wherein $R^7$ is an alcohol protecting group, with a catalyst and a second hydrogen reagent to prepare a compound of Formula (VII):

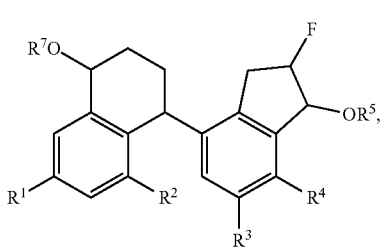
(VII)

wherein $R^7$ is an alcohol protecting group, and (b) contacting the compound of Formula (VII) with a deprotecting agent, thereby preparing the compound of Formula (V).

In some embodiments, the stereochemical outcome from the conversion of the compound of Formula (VI) to the compound of Formula (VII) is substrate controlled.

Any suitable deprotecting agent known in the art can be used to remove the $R^7$ alcohol protecting group. The deprotecting agent can be selected depending on the alcohol protecting group as known in the art.

In some embodiments, $R^7$ is a silyl protecting group. In some embodiments, the deprotecting agent is a fluoride reagent. In some embodiments, the deprotecting agent is tetra(n-butyl)ammonium fluoride.

In some embodiments, $R^7$ is an acyl protecting group. In some embodiments, the deprotecting agent is a reducing agent. In some embodiments, the reducing agent is DIBAL, lithium aluminum hydride or a borohydride. In some embodiments, the deprotecting agent is a base. In some embodiments, the base is a metal hydroxide (e.g., LiOH, NaOH, and KOH). In some embodiments, the deprotecting agent is an enzyme. In some embodiments, the enzyme is a hydrolase or a lipase.

In some embodiments, $R^7$ is a trityl protecting group or an ether protecting group. In some embodiments, the deprotecting agent is an acid. In some embodiments, the acid is HCl, formic acid, acetic acid, trifluoroacetic acid, or methanesulfonic acid. In some embodiments, the deprotecting agent is a Lewis acid. In some embodiments, the Lewis acid is $ZnCl_2$, $ZnBr_2$, $TiCl_4$, $BF_3$, or trimethylsilyl iodide (TMSI).

In some embodiments, $R^7$ is an ether protecting group. In some embodiments, the deprotecting agent is an acid. In some embodiments, the acid is HCl, formic acid, acetic acid, trifluoroacetic acid, or methanesulfonic acid.

In some embodiments, $R^7$ is an alkyl or benzyl protecting group. In some embodiments, the deprotecting agent is a reducing agent. In some embodiments, the reducing agent is DIBAL, lithium aluminum hydride or a borohydride. In some embodiments, the deprotecting agent is a Lewis acid. In some embodiments, the Lewis acid is $ZnCl_2$, $ZnBr_2$, $TiCl_4$, $BF_3$, or trimethylsilyl iodide (TMSI).

In some embodiments, $R^7$ is tert-butoxycarbonyl (Boc). In some embodiments, the deprotecting agent is an acid. In some embodiments, the acid is HCl, formic acid, acetic acid, trifluoroacetic acid, or methanesulfonic acid.

In some embodiments, the compound of Formula (VI) is purified from the previous palladium-mediated coupling reaction to prevent side reactions and/or an incomplete conversion in preparing the compound of Formula (VII). Accordingly, in some embodiments, the compound of Formula (VI) comprises less than 1000 ppm palladium. For example, the compound of Formula (VI) can comprise less than 900 ppm, 800 ppm, 700 ppm, 600 ppm, 500 ppm, 400 ppm, 300 ppm, 200 ppm, or less than 100 ppm palladium.

In some embodiments, the catalyst used to prepare a compound of Formula (VII) from a compound of Formula (VI) is a palladium-based or a platinum-based hydrogenation catalyst. In some embodiments, the catalyst is palladium on carbon or platinum on carbon. For example, the catalyst can be palladium on carbon. The palladium on carbon or platinum on carbon can be at any suitable concentration, for example, 5%, 10%, 20%, 30%, 40%, or 50% metal on carbon (weight/weight).

Any suitable hydrogen reagent can be used in combination with a suitable catalyst in the preparation of the compound of Formula (VII) from a compound of Formula (VI). In some embodiments, the second hydrogen reagent is hydrogen gas or formic acid. In some embodiments, the second hydrogen reagent is hydrogen gas.

Any suitable solvent can be used in preparing the compound of Formula (VII) in the processes described herein. Exemplary solvents include esters (e.g., ethyl acetate, isobutyl acetate, butyl acetate, etc), ethers (diethyl ether, methyl tert-butyl ether, tetrahydrofuran, 2-methyltetrahydrofuran, 1,4-dioxane, etc.), aliphatic hydrocarbons (e.g., pentane, hexane, etc.), polar protic solvents (e.g., water, ethanol, methanol, formic acid, etc.), or any combinations thereof. In some embodiments, the process further comprises a solvent that is methanol, ethanol, n-propanol, isopropanol, acetonitrile, tetrahydrofuran (THF), 2-methyltetrahydrofuran, diethyl ether, methyl tert-butyl ether, or a combination thereof. In some embodiments, the process further comprises a solvent that is methanol.

Any suitable temperature can be used in preparing the compound of Formula (VII). In some embodiments, the process further comprises a temperature of from about −78° C. to about 60° C. In some embodiments, the process further comprises a temperature of from about −20° C. to about 50° C. In some embodiments, the process further comprises a temperature of from about 0° C. to about 50° C. In some embodiments, the process further comprises a temperature of from about 20° C. to about 30° C. In some embodiments, the process further comprises a temperature of about 25° C.

The processes of the present disclosure can provide the compound of Formula (VII) in a yield of at least 50%, 55%, 60%, 65%, 70%, 75%, 80%, 85%, 90%, 95%, 97%, 98%, or at least 99%. In some embodiments, the yield of the compound of Formula (VII) is from about 60% to about 100%. In some embodiments, the yield of the compound of Formula (VII) is from about 70% to about 80% or from about 75% to about 85%. In some embodiments, the yield of the compound of Formula (VII) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (VII) is from about 60% to about 90%. In some embodiments, the yield of the compound of Formula (VII) is from about 60% to about 80%. In some embodiments, the yield of the compound of Formula (VII) is from about 60% to about 70%. In some embodiments, the yield of the compound of Formula (VII) is from about 70% to about 90%. In some embodiments, the yield of the compound of Formula (VII) is from about 70% to about 80%.

The processes of the present disclosure can provide the compound of Formula (VII) in a purity of from about 70% to about 100%, such as from about 75% to about 100%, from about 80% to about 100%, from about 85% to about 100%, from about 90% to about 100%, from about 95% to about 100%, or from about 98% to about 100%.

Any suitable solvent can be used in preparing the compound of Formula (V) in the processes described herein. Exemplary solvents include nitriles (e.g., acetonitrile, butyronitrile, etc.), esters (e.g., ethyl acetate, isobutyl acetate, butyl acetate, etc), ethers (diethyl ether, methyl tert-butyl ether, tetrahydrofuran, 2-methyltetrahydrofuran, 1,4-dioxane, etc.), aromatic hydrocarbons (e.g., toluene, benzene, xylenes, etc.), aliphatic hydrocarbons (e.g., pentane, hexane, etc.), polar aprotic solvents (e.g., dimethyl sulfoxide, dimethylformamide, etc.), polar protic solvents (e.g., water, ethanol, methanol, formic acid, etc.), or any combinations thereof. In some embodiments, the process further comprises a solvent that is an ether solvent or a chlorinated solvent. In some embodiments, the process further comprises a solvent that is tetrahydrofuran (THF), 2-methyltetrahydrofuran, diethyl ether, methyl tert-butyl ether, cyclopentyl methyl ether, toluene, benzene, n-heptane, or a combination thereof. In some embodiments, the process further comprises a solvent that is acetonitrile. In some embodiments, the process further comprises a solvent that is tetrahydrofuran (THF).

Any suitable temperature can be used in preparing the compound of Formula (V). In some embodiments, the process further comprises a temperature of from about −78° C. to about 60° C. In some embodiments, the process further comprises a temperature of from about −20° C. to about 50° C. In some embodiments, the process further comprises a temperature of from about 0° C. to about 50° C. In some embodiments, the process further comprises a temperature of from about −10° C. to about 10° C. In some embodiments, the process further comprises a temperature of about 0° C.

The processes of the present disclosure can provide the compound of Formula (V) in a yield of at least 50%, 55%, 60%, 65%, 70%, 75%, 80%, 85%, 90%, 95%, 97%, 98%, or at least 99%. In some embodiments, the yield of the compound of Formula (V) is from about 60% to about 100%. In some embodiments, the yield of the compound of Formula (V) is from about 70% to about 80% or from about 75% to about 85%. In some embodiments, the yield of the compound of Formula (V) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (V) is from about 60% to about 90%. In some embodiments, the yield of the compound of Formula (V) is from about 60% to about 80%. In some embodiments, the yield of the compound of Formula (V) is from about 60% to about 70%. In some embodiments, the yield of the compound of Formula (V) is from about 70% to about 90%. In some embodiments, the yield of the compound of Formula (V) is from about 70% to about 80%.

The processes of the present disclosure can provide the compound of Formula (V) in a purity of from about 70% to about 100%, such as from about 75% to about 100%, from about 80% to about 100%, from about 85% to about 100%, from about 90% to about 100%, from about 95% to about 100%, or from about 98% to about 100%.

In some embodiments, the process further comprises preparing the compound of Formula (VI) as described herein.

Further provided herein is a process, the process comprising preparing a compound of Formula (VI), the process comprising combining a compound of Formula (VIII):

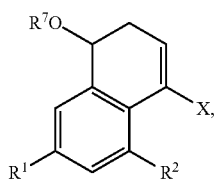

(VIII)

wherein X is —Br, —I, or -OTf;
a compound of Formula (IX):

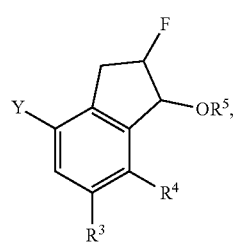

(IX)

wherein Y is —B(OH)$_2$, —B(OMe)$_2$, —B(OEt)$_2$, or -Bpin; and a palladium catalyst; to prepare the compound of Formula (VI):

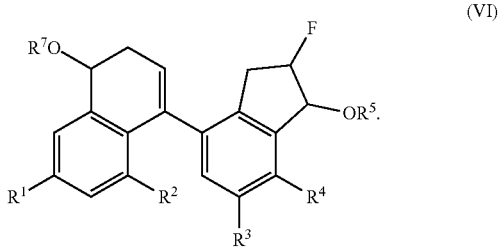

(VI)

In some embodiments of the processes of the disclosure, X is -OTf.

In some embodiments of the processes of the disclosure, Y is pinacolboranyl (Bpin).

Any suitable palladium catalyst known in the art can be used to prepare the compound of Formula (VI) from the compound of Formula (VIII) and the compound of Formula (IX). In some embodiments, the palladium catalyst is [1,2-bis(diphenylphosphino)ethane]dichloropalladium(II) (Pd(dppe)Cl$_2$), (1,3-bis(diphenylphosphino)propane)palladium(II) chloride (Pd(dppp)Cl$_2$), [1,1'-bis(diphenylphosphino)ferrocene]dichloropalladium(II) (Pd(dppf)Cl$_2$), bis(triphenylphosphine)palladium(II) dichloride (Pd(PPh$_3$)$_2$Cl$_2$), or tetrakis(triphenylphosphine)palladium(0) (Pd(PPh$_3$)$_4$). For example, the palladium catalyst can be Pd(dppf)Cl$_2$.

In some embodiments of the processes of the disclosure, R$^7$ is a silyl protecting group, such as a trialkylsilyl or a triarylsilyl protecting group. In some embodiments, R$^7$ is trimethylsilyl (TMS), triethylsilyl (TES), triisopropylsilyl (TIPS), triphenylsilyl (TPS), or tert-butyldimethylsilyl (TBS). For example, R$^7$ can be tert-butyldimethylsilyl (TBS).

In some embodiments of the process of the disclosure, R$^7$ is an ether, alkyl, trityl, acyl, or benzyl protecting group. In some embodiments, R$^7$ is an ether protecting group. In some embodiments, R$^7$ is methoxymethyl (MOM), methoxyethoxymethyl (MEM), benzyloxymethyl (BOM), or tetrahydropyranyl (THP). In some embodiments, R$^7$ is an alkyl protecting group. In some embodiments, R$^7$ is methyl, ethyl, isopropyl, or tert-butyl. In some embodiments, R$^7$ is a trityl protecting group. In some embodiments, R$^7$ is trityl (Tr), 4-monomethoxytrityl (MMTr), or 4,4'-dimethoxytrityl (DMTr). In some embodiments, R$^7$ an acyl protecting group. In some embodiments, R$^7$ is acetyl (Ac), benzoyl (Bz), or pivaloyl (Piv). In some embodiments, R$^7$ is tert-butoxycarbanyl (Boc). In some embodiments, R$^7$ is a benzyl protecting group. In some embodiments, R$^7$ is benzyl, or p-methoxybenzyl (PMB).

Any suitable solvent can be used in preparing the compound of Formula (VI) in the processes described herein. Exemplary solvents include ethers (diethyl ether, methyl tert-butyl ether, tetrahydrofuran, 2-methyltetrahydrofuran, 1,4-dioxane, etc.), aromatic hydrocarbons (e.g., toluene, benzene, xylenes, etc.), polar aprotic solvents (e.g., dimethyl sulfoxide, dimethylformamide, etc.), or any combinations thereof. In some embodiments, the process further comprises a solvent that is a protic solvent, an ether solvent, and/or an aromatic hydrocarbon solvent. In some embodiments, the process further comprises a solvent that is water, methanol, dioxane, tetrahydrofuran (THF), 2-methyltetrahydrofuran, diethyl ether, methyl tert-butyl ether, cyclopentyl methyl ether, benzene, toluene, n-heptane, or a combination thereof. In some embodiments, the process further comprises a solvent that is THF, 1,4-dioxane, or dimethylformamide. In some embodiments, the solvent further comprises water. In some embodiments, the process further comprises a solvent that is water and dioxane.

Any suitable temperature can be used in preparing the compound of Formula (VI). In some embodiments, the process further comprises a temperature of from about 0° C. to about 100° C. In some embodiments, the process further comprises a temperature of from about 20° C. to about 100° C. In some embodiments, the process further comprises a temperature of from about 50° C. to about 100° C. In some embodiments, the process further comprises a temperature of from about 70° C. to about 90° C. In some embodiments, the process further comprises a temperature of about 80° C.

In some embodiments, the process further comprises purifying the compound of Formula (VI). In some embodiments, the purifying comprises removing the palladium catalyst by a palladium scavenging agent. Any suitable palladium scavenging agent known in the art can be used to purify the compound of Formula (VI). For example, SiliaMetS series of metal scavengers (SiliCycle, Quebec City, Quebec, Canada), functionalized silica gels designed to react and bind metal, such as SiliaMetS Thiol, SiliaMetS DMT, SiliaMetS Amine, SiliaMetS Diamine, or SiliaMetS Triamine, can be used to remove the palladium catalyst. In some embodiments, the process comprises purifying the compound of Formula (VI) by treating with SiliaMetS DMT. In some embodiments, the compound of Formula (VI) comprises less than 1000 ppm palladium, such as less than 900 ppm, 800 ppm, 700 ppm, 600 ppm, 500 ppm, 400 ppm, 300 ppm, 200 ppm, or less than 100 ppm palladium.

In some embodiments of the processes of the disclosure, $R^1$ is —F.

In some embodiments of the processes of the disclosure, $R^2$ is —CN.

In some embodiments of the processes of the disclosure, $R^3$ is —H.

In some embodiments of the processes of the disclosure, $R^4$ is —S(O)$_2$CH$_3$.

In some embodiments of the processes of the disclosure, $R^5$ is an ether, alkyl, trityl, or benzyl protecting group. In some embodiments, $R^5$ is methoxymethyl (MOM), 2-methoxyethoxymethyl (MEM), tetrahydropyranyl (THP), tert-butyl, allyl, benzyl, 2-methoxybenzyl, 3-methoxybenzyl, or 4-methoxybenzyl. In some embodiments, $R^5$ is methoxymethyl (MOM).

In some embodiments, the process comprises: (a) contacting the compound of Formula (Ia) or (Ib):

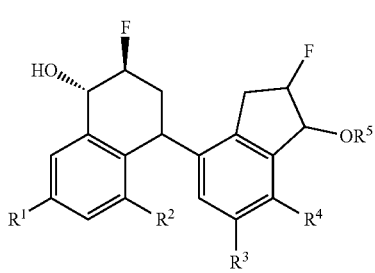

(Ia)

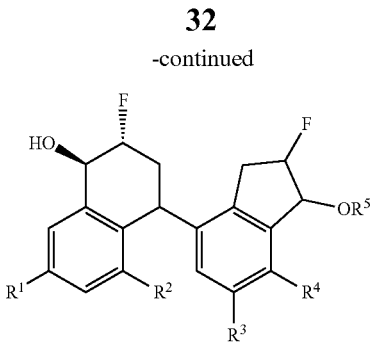

(Ib)

with a fluorinating agent to prepare a compound of Formula (XIa) or (XIb):

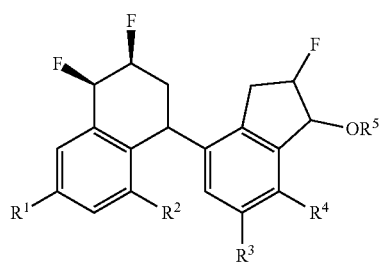

(XIa)

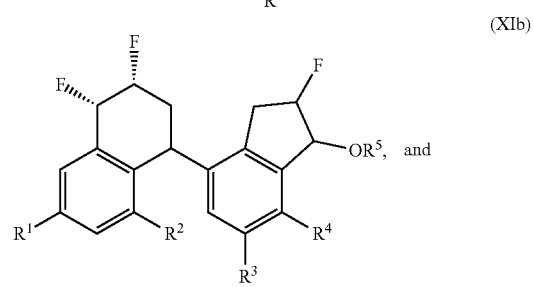

(XIb), and (b) contacting the compound of Formula (XIa) or (XIb) with a second deprotecting agent, to prepare a compound of Formula (Xa) or (Xb):

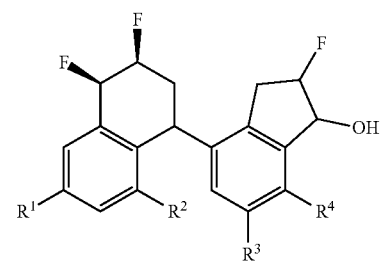

(Xa)

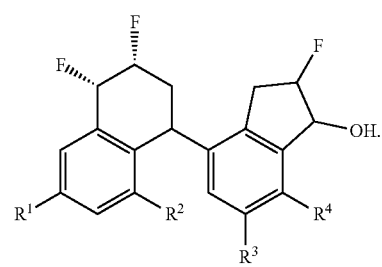

(Xb)

In some embodiments, the fluorinating agent is a nucleophilic fluorinating agent. Any suitable nucleophilic fluorinating agent known in the art can be used to prepare the compound of Formula (XIa) or (XIb). See, Ni, C. et al. *Chem. Rev.* 2015, 115, 2, 765-825. Nucleophilic fluorinating agents include diethylaminosulfur trifluoride (DAST), sulfur tetrafluoride, bis(2-methoxyethyl)aminosulfur trifluoride (Deoxo-Fluor®), 4-tert-butyl-2,6-dimethylphenylsulfur trifluoride (Fluolead™), morpholinodifluorosulfinium tetrafluoroborate (XtalFluor-M®), N,N-diethylamino-S,S-difluorosulfinium tetrafluoroborate (XtalFluor-E®), pyridine-2-sulfonyl fluoride (PyFluor), PhenoFluor™, AlkylFluor™, morpholinosulfur trifluoride (morph-DAST), nonafluorobutanesulfonyl fluoride, 4-(trifluoromethyl)benzenesulfonyl fluoride, N,N-diethyl-α,α-difluoro-3-methylbenzylamine (DFMBA), tetramethylfluoroformamidinium hexafluorophosphate (TFFH), 3,3-difluoro-1,2-diphenylcyclopropene, and tetrabutylammonium bifluoride (TBABF). In some embodiments, the fluorinating agent is sulfur tetrafluoride, diethylaminosulfur trifluoride, [bis(2-methoxyethyl)amino]sulfur trifluoride, or N,N-diethyl-1,1,2,3,3,3-hexafluoropropylamine (Ishikawa's reagent). In some embodiments, the fluorinating agent is diethylaminosulfur trifluoride.

In some embodiments, the compound of Formula (Ia) or (Ib) is contacted with a fluorinating agent in the presence of an N-silyl secondary amine. In some embodiments, the N-silyl secondary amine is N-(trimethylsilyl)pyrrolidine, N-(trimethylsilyl)piperidine, or N-(trimethylsilyl)morpholine. In one embodiment, the N-silyl secondary amine is N-(trimethylsilyl)morpholine. Without wishing to be bound by theory, the presence of the N-silyl secondary amine improves the diastereoselectivity of the transformation. In some embodiments, the trans/cis diastereoselectivity is at least 10:1, such as, 10:1, 11:1, 12:1, 13:1, 14:1, 15:1, 16:1, 17:1, 18:1, 19:1, 20:1, or more.

Any suitable solvent can be used in preparing the compound of Formula (XIa) or (XIb) in the processes described herein. Exemplary solvents include nitriles (e.g., acetonitrile, butyronitrile, etc.), esters (e.g., ethyl acetate, isobutyl acetate, butyl acetate, etc), ethers (diethyl ether, methyl tert-butyl ether, tetrahydrofuran, 2-methyltetrahydrofuran, 1,4-dioxane, etc.), aromatic hydrocarbons (e.g., toluene, benzene, xylenes, etc.), polar aprotic solvents (e.g., dimethyl sulfoxide, dimethylformamide, etc.), chlorinated solvents (e.g., chloroform, dichloromethane, dichloroethane, etc.), or any combinations thereof. In some embodiments, the process further comprises a solvent that is an ether solvent, and/or a chlorinated solvent. In some embodiments, the process further comprises a solvent that is water, methanol, dioxane, tetrahydrofuran (THF), 2-methyltetrahydrofuran, methyl tert-butyl ether, cyclopentyl methyl ether, toluene, n-heptane, 1,2-dichloroethane, chloroform, or chlorobenzene, or a combination thereof. In some embodiments, the process further comprises a solvent that is dichloromethane.

Any suitable temperature can be used in preparing the compound of Formula (XIa) or (XIb). In some embodiments, the process further comprises a temperature of from about −78° C. to about 40° C. In some embodiments, the process further comprises a temperature of from about −50° C. to about 20° C. In some embodiments, the process further comprises a temperature of from about −40° C. to about −10° C.

Any suitable second deprotecting agent known in the art can be used to remove the $R^5$ alcohol protecting group. The second deprotecting agent can be selected depending on the alcohol protecting group as known in the art. In some embodiments, $R^5$ is an ether protecting group. In some embodiments, the second deprotecting agent is an inorganic acid, such as hydrogen chloride.

Any suitable solvent can be used in preparing the compound of Formula (Xa) or (Xb) in the processes described herein. Exemplary solvents include nitriles (e.g., acetonitrile, butyronitrile, etc.), esters (e.g., ethyl acetate, isobutyl acetate, butyl acetate, etc.), ethers (diethyl ether, methyl tert-butyl ether, tetrahydrofuran, 2-methyltetrahydrofuran, 1,4-dioxane, etc.), aromatic hydrocarbons (e.g., toluene, benzene, xylenes, etc.), polar aprotic solvents (e.g., dimethyl sulfoxide, dimethylformamide, etc.), polar protic solvents (e.g., water, ethanol, methanol, formic acid etc.), chlorinated solvents (e.g., chloroform, dichloromethane, dichloroethane, etc.), or any combinations thereof. In some embodiments, the process further comprises a solvent that is a protic solvent, an ether solvent, and/or a chlorinated solvent. In some embodiments, the process further comprises a solvent that is water, methanol, dioxane, tetrahydrofuran (THF), 2-methyltetrahydrofuran, diethyl ether, methyl tert-butyl ether, cyclopentyl methyl ether, benzene, toluene, n-heptane, 1,2-dichloroethane, dichloromethane, chloroform, or chlorobenzene, or a combination thereof. In some embodiments, the process further comprises a solvent that is tetrahydrofuran.

Any suitable temperature can be used in preparing the compound of Formula (Xa) or (Xb). In some embodiments, the process further comprises a temperature of from about −40° C. to about 70° C. In some embodiments, the process further comprises a temperature of from about 0° C. to about 40° C. In some embodiments, the process further comprises a temperature of from about 20° C. to about 40° C. In some embodiments, the process further comprises a temperature of about 30° C.

In some embodiments, the process comprises: (a) contacting the compound of Formula (Ia) with a fluorinating agent to prepare a compound of Formula (XIa), and (b) contacting the compound of Formula (XIa) with a second deprotecting agent, to prepare a compound of Formula (Xa).

In some embodiments, the process comprises: (a) contacting the compound of Formula (Ib) with a fluorinating agent to prepare a compound of Formula (XIb), and (b) contacting the compound of Formula (XIb) with a second deprotecting agent, to prepare a compound of Formula (Xb).

In some embodiments, the compound of Formula (Xa) is a compound of Formula (Xa-1), (Xa-2), and/or (Xa-3):

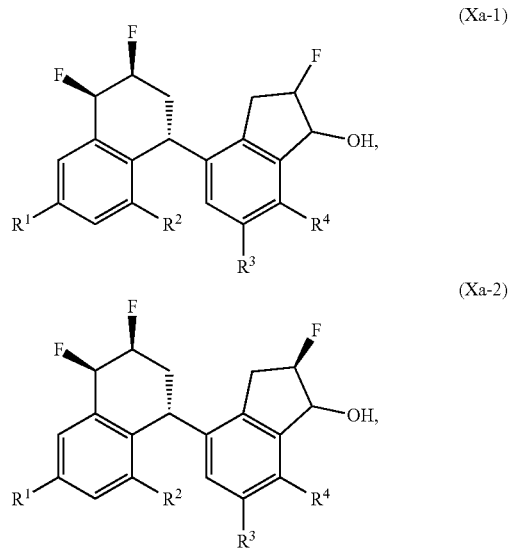

(Xa-3)

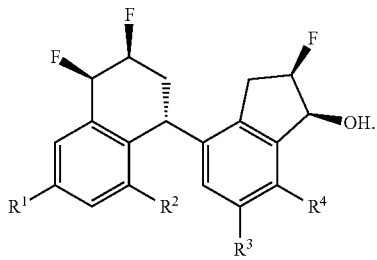

In some embodiments, the compound of Formula (Xa) is a compound of Formula (Xa-3) that is substantially free of other stereoisomers. In some embodiments, the compound of Formula (Xa) has the structure:

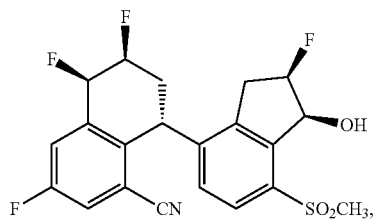

that is substantially free of other stereoisomers.

Further provided herein is a process of preparing a compound of Formula (Xa) or (Xb):

(Xa)

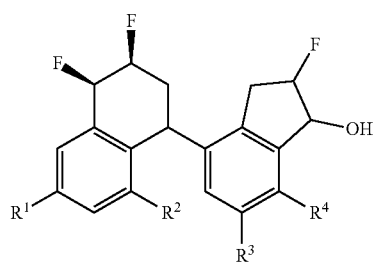

(Xb)

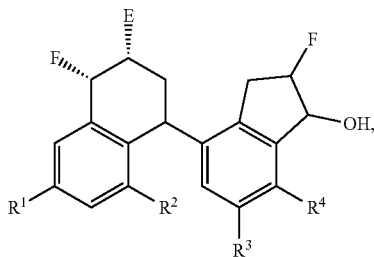

wherein:
R¹ and R² are independently selected from —H, —F, —Cl, and —CN;
R³ is H, F, or Cl; and
R⁴ is selected from the group consisting of —H, —F, —Cl, —C₁-C₃ alkyl, and —S(O)₂(C₁-C₃ alkyl), wherein the —C₁-C₃ alkyl or —S(O)₂(C₁-C₃ alkyl) is optionally substituted with 1-3 halogen; the process comprising: (a) contacting a compound of Formula (Ia) or (Ib):

(Ia)

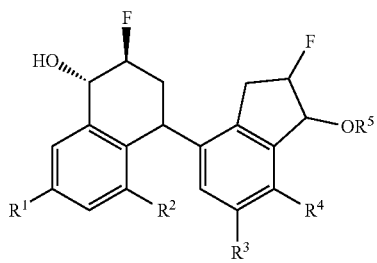

(Ib)

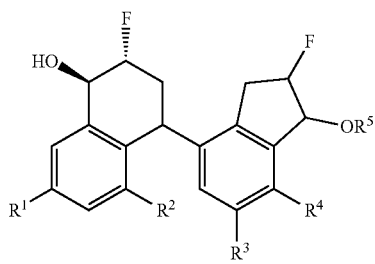

wherein R⁵ is an alcohol protecting group, with a fluorinating agent to prepare a compound of Formula (XIa) or (XIb):

(XIa)

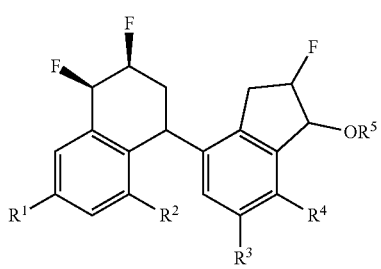

(XIb)

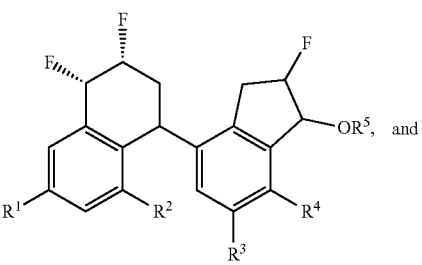

(b) contacting the compound of Formula (XIa) or (XIa) with a deprotecting agent, thereby preparing the compound of Formula (Xa) or (Xb); wherein the compound of Formula (Xa) or (Xb) is prepared in at least a 10 g scale.

In some embodiments, R⁵ is an ether, alkyl, trityl, or benzyl protecting group. In some embodiments, R⁵ is methoxymethyl (MOM), 2-methoxyethoxymethyl (MEM), tetrahydropyranyl (THP), tert-butyl, allyl, benzyl, 2-methoxybenzyl, 3-methoxybenzyl, or 4-methoxybenzyl. In some embodiments, R⁵ is methoxymethyl (MOM).

In some embodiments, the fluorinating agent is a nucleophilic fluorinating agent. In some embodiments, the fluorinating agent is sulfur tetrafluoride, diethylaminosulfur trifluoride, [bis(2-methoxyethyl)amino]sulfur trifluoride, or N,N-diethyl-1,1,2,3,3,3-hexafluoropropylamine. In some embodiments, the fluorinating agent is diethylaminosulfur trifluoride.

In some embodiments, the process comprises: (a) contacting the compound of Formula (Ia) with a fluorinating agent to prepare a compound of Formula (XIa), and (b) contacting the compound of Formula (XIa) with a second deprotecting agent, to prepare a compound of Formula (Xa).

In some embodiments, the process comprises: (a) contacting the compound of Formula (Ib) with a fluorinating agent to prepare a compound of Formula (XIb), and (b) contacting the compound of Formula (XIb) with a second deprotecting agent, to prepare a compound of Formula (Xb).

In some embodiments, the compound of Formula (Xa) is a compound of Formula (Xa-1), (Xa-2), and/or (Xa-3). In some embodiments, the compound of Formula (Xa) is a compound of Formula (Xa-3) that is substantially free of other stereoisomers. In some embodiments, the compound of Formula (Xa) has the structure:

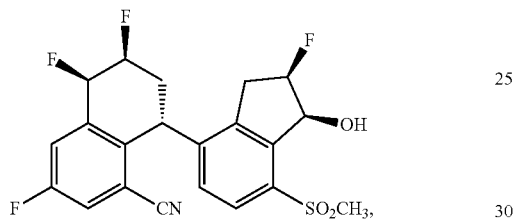

that is substantially free of other stereoisomers.

In some embodiments, the compound of Formula (Ia) or (Ib) is prepared by any process described herein.

Further provided herein is a process of preparing a compound of Formula (Xa) or (Xb):

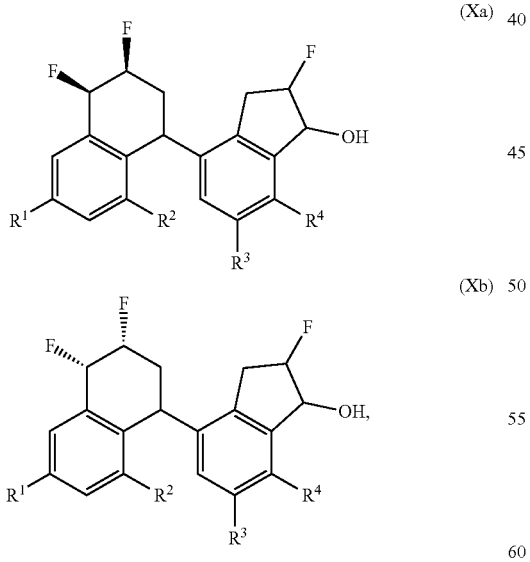

wherein:
R$^1$ and R$^2$ are independently selected from —H, —F, —Cl, and —CN;
R$^3$ is —H, —F, or —Cl; and
R$^4$ is selected from the group consisting of —H, —F, —Cl, —C$_1$-C$_3$ alkyl, and —S(O)$_2$(C$_1$-C$_3$ alkyl), wherein the —C$_1$-C$_3$ alkyl or —S(O)$_2$(C$_1$-C$_3$ alkyl) is optionally substituted with 1-3 halogen; the process comprising:

(a) combining a compound of Formula (VII):

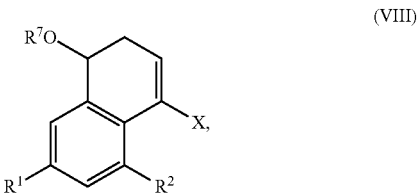

wherein X is —Br, —I, or -OTf, and R$^7$ is an alcohol protecting group;

a compound of Formula (IX):

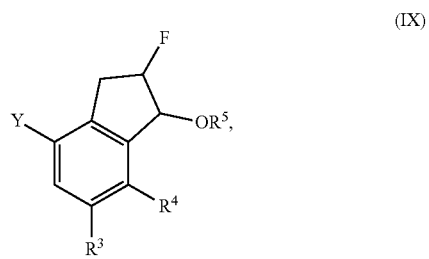

wherein Y is —B(OH)$_2$, —B(OMe)$_2$, —B(OEt)$_2$, or -Bpin; and a palladium catalyst; to prepare the compound of Formula (VI):

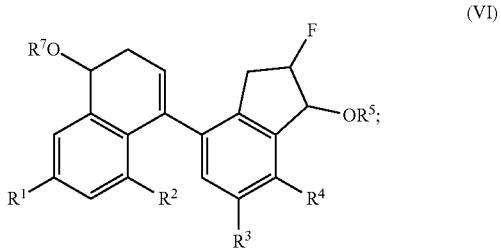

(b) contacting a compound of Formula (VI) with a catalyst and a third hydrogen reagent to prepare a compound of Formula (VII):

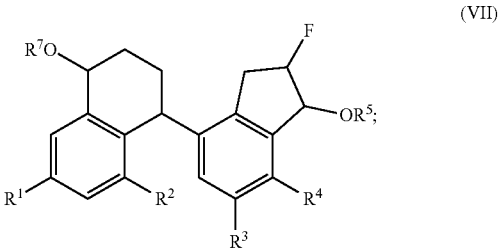

(c) contacting the compound of Formula (VII) with a third deprotecting agent, thereby preparing the compound of Formula (V):

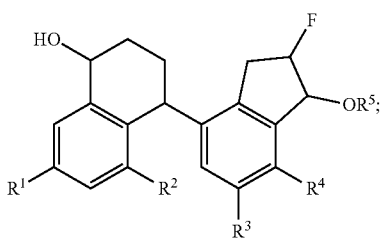

(V)

(d) contacting a compound of Formula (V) with an oxidizing agent to prepare the compound of Formula (IV):

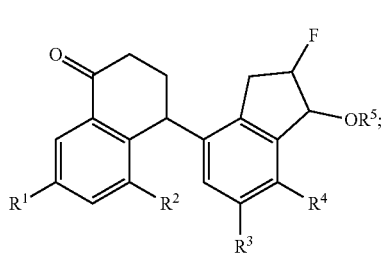

(IV)

(e) contacting a compound of Formula (IV) with a $R^6X$ reagent and a base, wherein $R^6$ is an alcohol protecting group, X is —Cl, —Br, —I, -OMs, -OTs, or -OTf, and the base is triethylamine, diisopropylethylamine, LDA, LiHMDS, NaHMDS, or KHMDS, to prepare the compound of Formula (III):

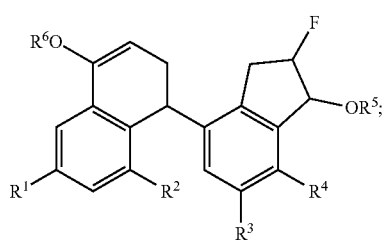

(III)

(f) contacting a compound of Formula (II) with an electrophilic fluorinating agent to prepare the compound of Formula (Ia) or (IIb):

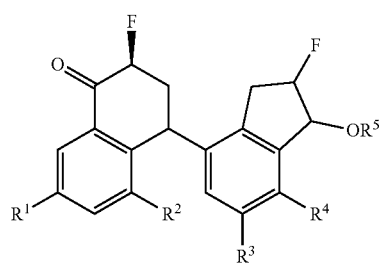

(IIa)

-continued

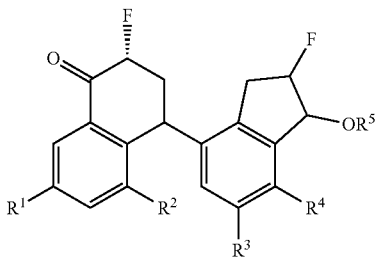

(IIb)

(g) contacting a compound of Formula (IIa) or (IIb) with a chiral ruthenium(II) catalyst and a fourth hydrogen reagent to prepare a compound of Formula (Ia) or (Ib):

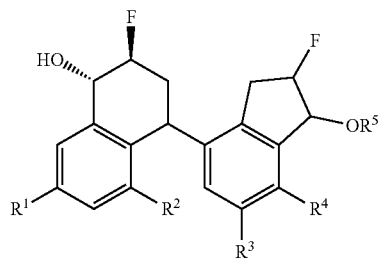

(Ia)

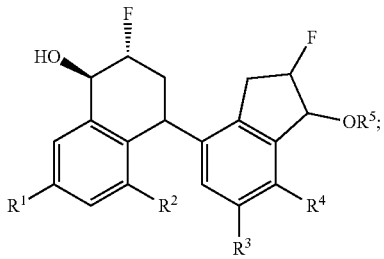

(Ib)

(h) contacting the compound of Formula (Ia) or (Ib) with a fluorinating agent to prepare a compound of Formula (XIa) or (XIb):

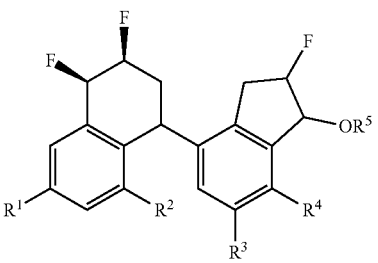

(XIa)

-continued

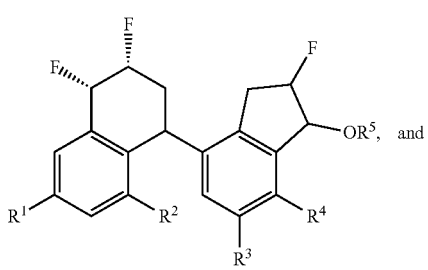
(XIb)

(i) contacting the compound of Formula (XIa) or (XIb) with a fourth deprotecting agent, to prepare a compound of Formula (Xa) or (Xb):

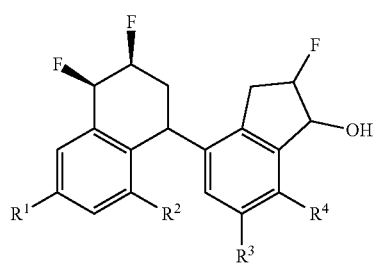
(Xa)

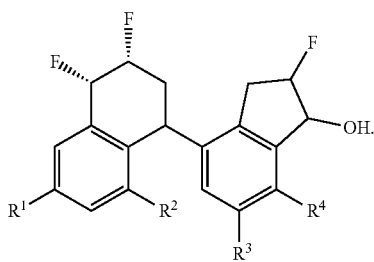
(Xb)

Any suitable third deprotecting agent known in the art can be used to remove the $R^7$ alcohol protecting group. The third deprotecting agent can be selected depending on the alcohol protecting group as known in the art. In some embodiments, $R^7$ is a silyl group, an ether group, an alkyl group, a trityl group, an acyl group, or a benzyl group. In some embodiments, the third deprotecting agent is a reducing agent, oxidizing agent, acid, Lewis acid, base, fluoride reagent, or enzyme.

In some embodiments, $R^7$ is a silyl protecting group. In some embodiments, the third deprotecting agent is a fluoride reagent, such as tetra(n-butyl)ammonium fluoride.

Any suitable fourth deprotecting agent known in the art can be used to remove the $R^5$ alcohol protecting group. The fourth deprotecting agent can be selected depending on the alcohol protecting group as known in the art. In some embodiments, $R^5$ is an ether protecting group. In some embodiments, the fourth deprotecting agent is an inorganic acid, such as hydrogen chloride.

The processes of the present disclosure can provide the compound of Formula (Xa) or Formula (Xb) in a yield of at least 50%, 55%, 60%, 65%, 70%, 75%, 80%, 85%, 90%, 95%, 97%, 98%, or at least 99%. In some embodiments, the yield of the compound of Formula (Xa) or Formula (Xb) is from about 60% to about 100%. In some embodiments, the yield of the compound of Formula (Xa) or Formula (Xb) is from about 70% to about 80% or from about 75% to about 85%. In some embodiments, the yield of the compound of Formula (Xa) or Formula (Xb) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (Xa) or Formula (Xb) is from about 60% to about 90%. In some embodiments, the yield of the compound of Formula (Xa) or Formula (Xb) is from about 70% to about 90%. In some embodiments, the yield of the compound of Formula (Xa) or Formula (Xb) is from about 70% to about 80%.

The processes of the present disclosure can provide the compound of Formula (Xa) or Formula (Xb) in a purity of from about 70% to about 100%, such as from about 75% to about 100%, from about 80% to about 100%, from about 85% to about 100%, from about 90% to about 100%, from about 95% to about 100%, or from about 98% to about 100%.

The processes of the present disclosure are amenable to synthesis of gram to kilogram quantities of the compound of Formula (Ia), (Ib), (IIa), (IIb), (III), (IV), (V), (VI), (VII), (VIII), (IX), (Xa), (Xb), (XIa), and/or (XIb) described herein. In some embodiments, the process comprises at least 10 g, 20 g, 30 g, 40 g, 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 500 kg, or at least 1000 kg or more, or a range between any two values of the foregoing, of the compound of Formula (Ia), (Ib), (IIa), (IIb), (III), (IV), (V), (VI), (VII), (VIII), (IX), (Xa), (Xb), (XIa), and/or (XIb).

EXAMPLES

Example 1: Synthesis of (5S,8R)-8-[(1S)-2,2-difluoro-1-hydroxy-7-(2-methylphenyl)-2,3-dihydro-1H-inden-4-yl]-3,5-difluoro-5,6,7,8-tetrahydronaphthalene-1-carbonitrile (Compound 1)

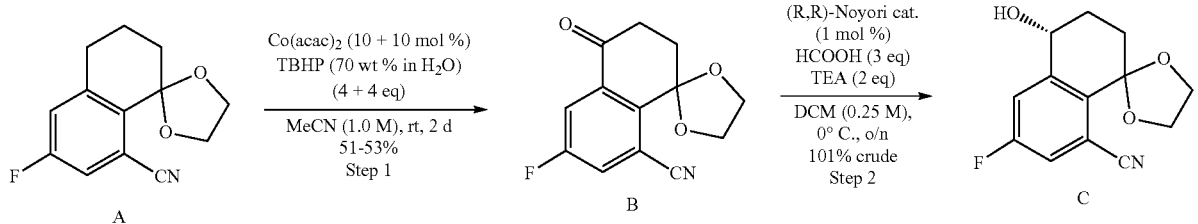

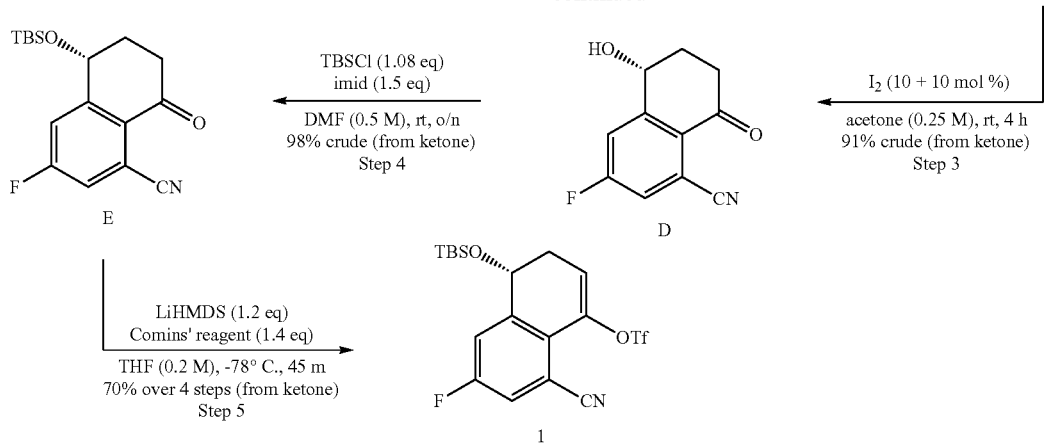

Step 1: Synthesis of Intermediate B

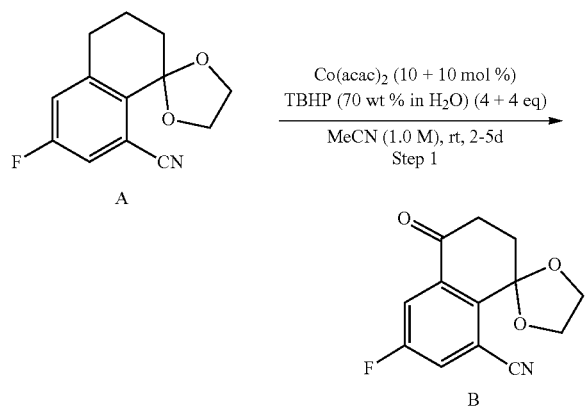

A 500 mL 3-neck round bottom flask (RBF) equipped with a stir bar in a room temperature water bath was charged with ketal A (15.0 g, 64.4 mmol, 1 eq), acetonitrile (MeCN, 65 mL, ~1.0 M), and Co(acac)2 (1.65 g, 6.44 mmol, 10 mol %), allowing the inclusion of air. Septa were placed in each side-arm. An empty balloon was inserted into one septum to capture oxygen generated during the reaction while a temperature probe was inserted into the other. An addition funnel was affixed to the middle neck and tert-butyl hydroperoxide (TBHP, 70 wt % in H$_2$O, 35.6 mL, 258 mmol, 4 eq) was added. A septum was placed in the top of the addition funnel and TBHP was subsequently added dropwise over ~1 hour during which the homogeneous mixture turns from red to dark green. Mild bubbling due to TBHP decomposition may be observed and the balloon will begin to fill. The reaction was then stirred at room temperature overnight. After stirring overnight (typically 40-50% conv. by crude NMR, solution turns greenish-brown), a second portion of Co(acac)$_2$ (1.65 g, 6.44 mmol, 10 mol %) was added and the addition funnel was refilled with TBHP (70 wt % in water, 35.6 mL, 258 mmol, 4 eq). The TBHP was once again added dropwise over ~1 hour and the solution was stirred overnight once again. After 2 days (typically 70-80% conv.), the reaction was diluted with EtOAc (~100 mL) and H$_2$O (~100 mL) and the organic layer was separated. The aqueous layer (heterogeneous) was extracted twice more with EtOAc (~125 mL) and the homogeneous organic layers were combined in a 1 L Erlenmeyer flask. With stirring, satd. Na$_2$S$_2$O$_3$ (~400 mL, >1.25 mol) was added over ~5 min. The resulting mixture was then stirred for 30 minutes. The organic layer was then separated and the aqueous layer back-extracted with EtOAc (~200 mL). All combined organic layers were dried (Na$_2$SO$_4$), filtered into a 1 L RBF, and concentrated to a crude dark colored wet solid. Ethanol (200 proof, ~40 mL) was added (some smoking observed) and the mixture was brought to near boiling via heat gun where it became homogeneous. This was allowed to cool to room temperature over 1-2 hours during which clumps of red needle-like crystals formed. The crystals were then filtered while washing with cold hexanes (~200 mL) to give intermediate B as a red crystalline solid (8.39 g, 53%, 92-96% pure).

Step 2: Synthesis of Intermediate C

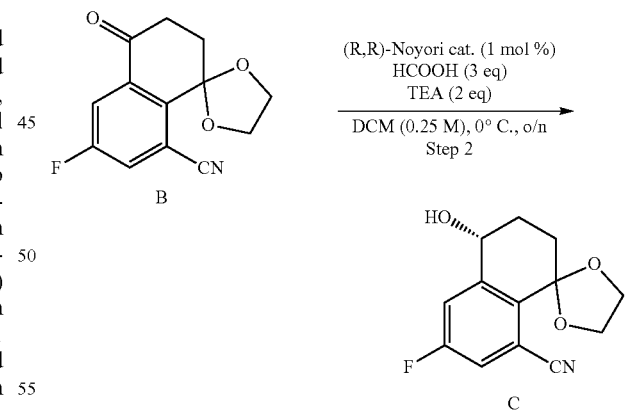

Intermediate B from the previous step (41.3 g, 167 mmol, 1.0 equiv, ~94% pure) was dissolved in dry dichloromethane (DCM, ~650 mL, ~0.25 M) and cooled to 0° C. Formic acid (18.9 mL, 502 mmol, 3 equiv) and Et$_3$N (46.3 mL, 334 mmol, 2 equiv) were added and the red homogeneous solution was degassed with N$_2$ for ~10 minutes. RuCl(p-cymene)[(R,R)-Ts-DPEN] (1.06 g, 1.67 mmol, 0.01 equiv.) was added and the reaction was stirred overnight at 4° C. (fridge) under N$_2$ atmosphere. Upon completion, the reaction was diluted with ~200 mL of DCM and washed with large amounts of water (3×1 L), which removed all Et₃N and formic acid by crude NMR. The organic layer was then dried over Na₂SO₄ and concentrated to afford the crude intermediate C as a red foam (42.2 g, 101%), including a small amount of DCM.

Step 3: Synthesis of Intermediate D

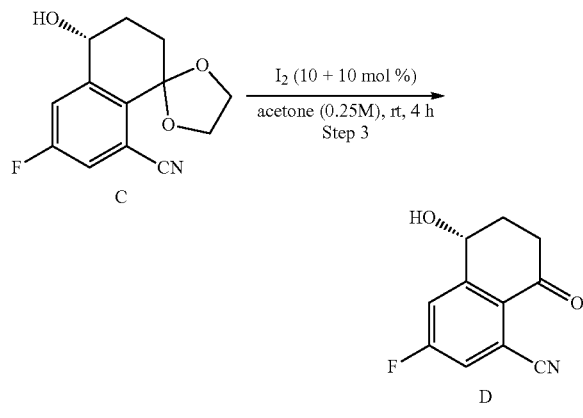

To the crude product of step 2 (42.2 g, ~167 mmol (ideal), 1.0 equiv) and acetone (~650 mL, ~0.25 M) at room temperature under N₂ atmosphere was added I₂ (4.24 g, 16.7 mmol, 0.1 equiv). The reaction mixture was stirred at room temperature for 2 hours. A second batch of I₂ (4.24 g, 16.7 mmol, 0.1 equiv) was added and the reaction was stirred for an additional 2 hours. After 4 hours total, the reaction was complete by liquid chromatography-mass spectrometry (LCMS) and subsequently quenched with saturated Na₂S₂O₃ (~200 mL). The mixture was extracted with EtOAc (2×~200 mL), dried over Na₂SO₄, and concentrated. Significant quantities of water remained after concentration so the mixture was taken back up in EtOAc (~600 mL) and dried once more with Na₂SO₄. The dry solution was finally concentrated to afford the crude intermediate D (31.5 g, 91% crude from ketone) as a red/black solid.

Step 4: Synthesis of Intermediate E

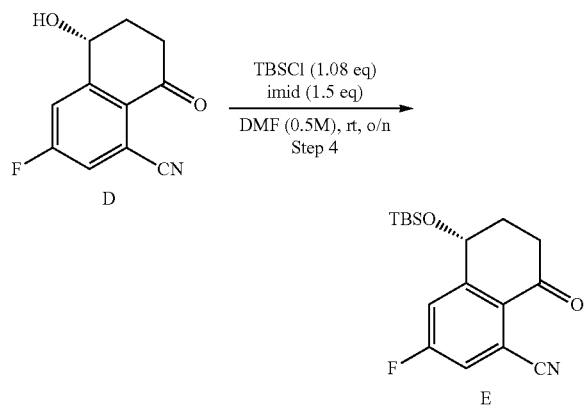

To the crude product from step 3 (31.5 g, 154 mmol, 1 equiv) in dry DMF (~300 mL, ~0.5 M) at room temperature under N₂ atmosphere was added imidazole (15.7 g, 231 mmol, 1.5 equiv) in one portion. TBSCl (25.0 g, 166 mmol, 1.08 equiv) was then added in 4 portions over ~10 minutes and the mixture was stirred at room temperature overnight. After stirring overnight, crude NMR indicated 100% conv. (~96% conv. by LCMS) and the reaction was quenched with MeOH (~50 mL) and diluted with EtOAc (~600 mL). This was washed with large amounts of water (3×1 L), dried over Na₂SO₄, and concentrated to afford the crude TBS ether (51.9 g, 98% crude from ketone) as a red/black solid. A small quantity of crude material was purified by column chromatography (SiO₂, hexanes to 15% EtOAc) and the enantiopurity was determined by analytical chiral HPLC (OD-H column, 15% iPrOH in hexanes, $t_1$=8.46 min) against a racemic sample that was obtained using NaBH₄ in the reduction step 2.

Step 5: Synthesis of Compound 1

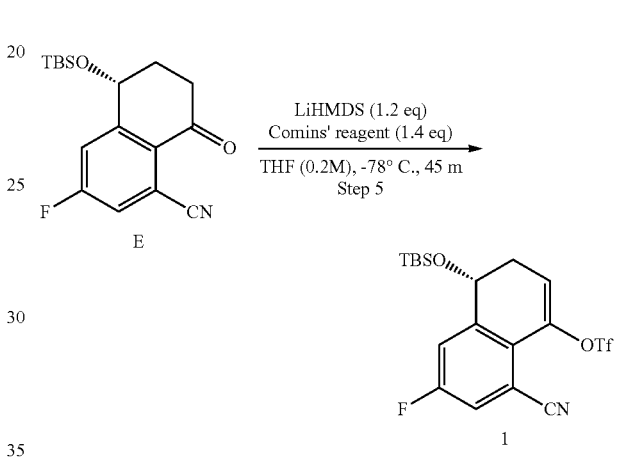

A mixture of the intermediate E (30.0 g, 94 mmol) and Comins' reagent (51.7 g, 132 mmol) in THF (470 mL) was placed in a 1 L single neck round bottom flask equipped with magnetic stirring bar and nitrogen inlet. The mixture was cooled under nitrogen to −78° C. and a solution of LiHMDS (98.6 mL, 98.6 mmol, 1M solution in THF) was added dropwise via syringe over 10 min. The resulting solution was stirred for 1 h at −78° C. and quenched at −78° C. with 3M aqueous solution of N,N-dimethylethylenediamine (5.6 mL, 66 mmol in 22 mL of water). The cooling bath was removed, and the reaction was stirred at ambient temperature for 1 h. Once TLC analysis indicated complete consumption of Comins' reagent, the reaction was concentrated to dryness under reduced pressure. The residue was partitioned between hexanes (400 mL) and 3M aq. NaOH (400 mL). The dark brown aqueous phase was separated and additionally extracted with hexanes (150 mL). The combined organic extract was additionally washed with 3M NaOH (2×100 mL), 1M HCl (300 mL, substantial decolorization was observed) and brine (300 mL). The hexanes solution was dried over Na₂SO₄, mixed with 7.5 g of activated charcoal and stirred overnight at room temperature. The resulting suspension was stirred through a celite plug and concentrated to dryness. The residual oil was seeded with the product to induce crystallization, which provided 33.4 g (79% yield) of Compound 1 as a yellow solid. $^1$H NMR (400 MHZ, Chloroform-d) δ 7.44 (ddd, J=8.5, 2.7, 1.1 Hz, 1H), 7.34 (ddd, J=7.9, 2.7, 0.8 Hz, 1H), 6.23 (dd, J=6.5, 3.7 Hz, 1H), 4.84 (ddd, J=12.0, 6.9, 1.0 Hz, 1H), 2.64-2.47 (m, 2H), 0.96 (s, 9H), 0.18 (s, 3H), 0.15 (s, 3H).

Example 2: Synthesis of (5R,6S,8R)-3,5,6-trifluoro-8-[(1S,2R)-2-fluoro-1-hydroxy-7-methanesulfonyl-2,3-dihydro-1H-inden-4-yl]-5,6,7,8-tetrahydronaphthalene-1-carbonitrile
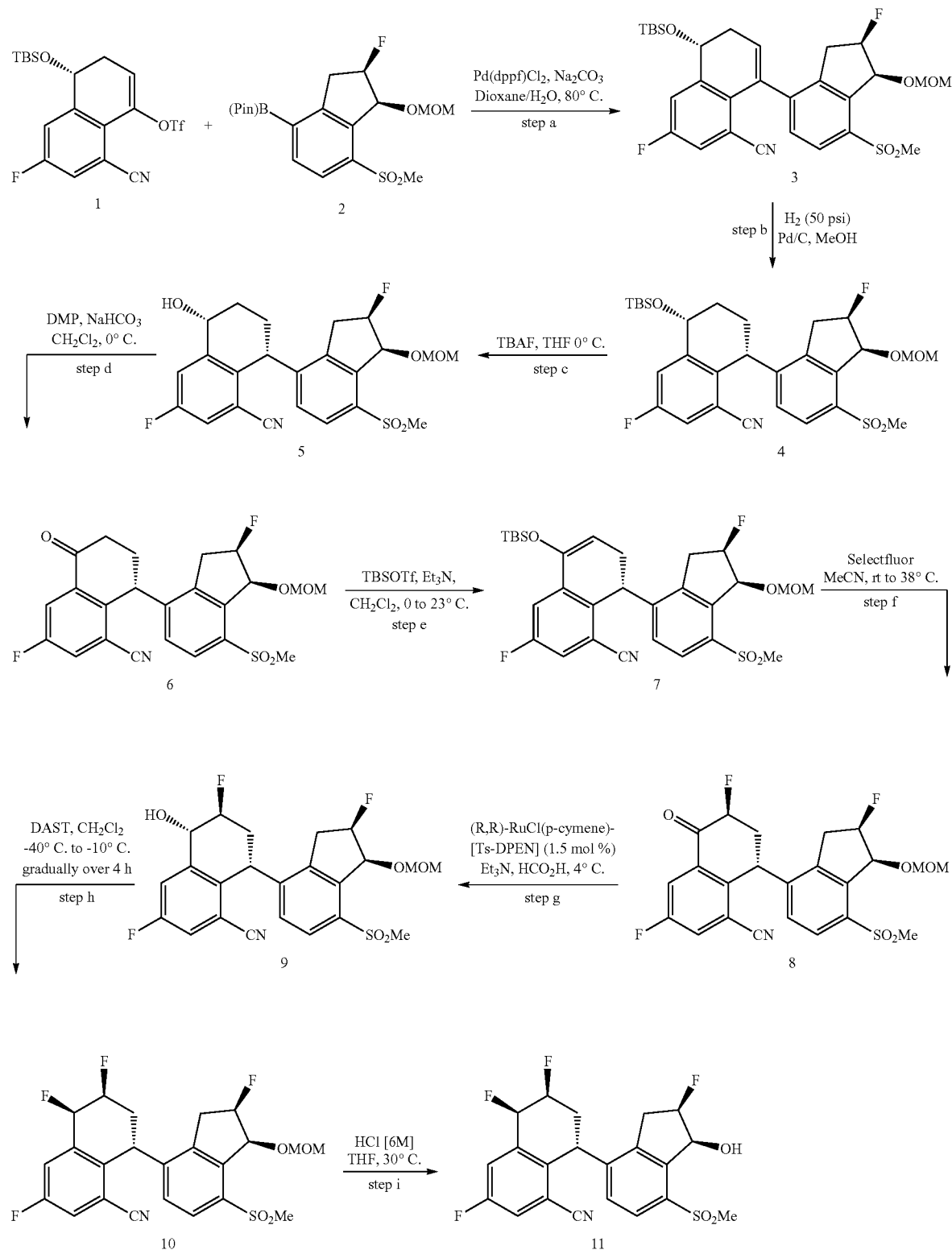

Step a: Synthesis of Compound 3

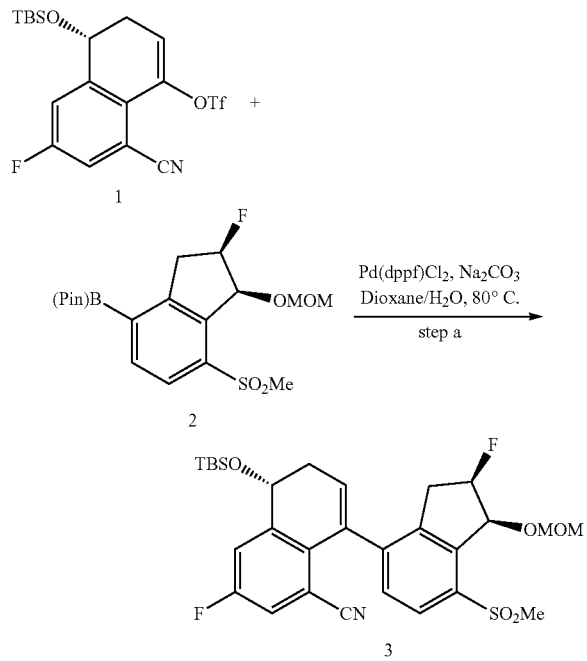

Step b: Synthesis of Compound 4

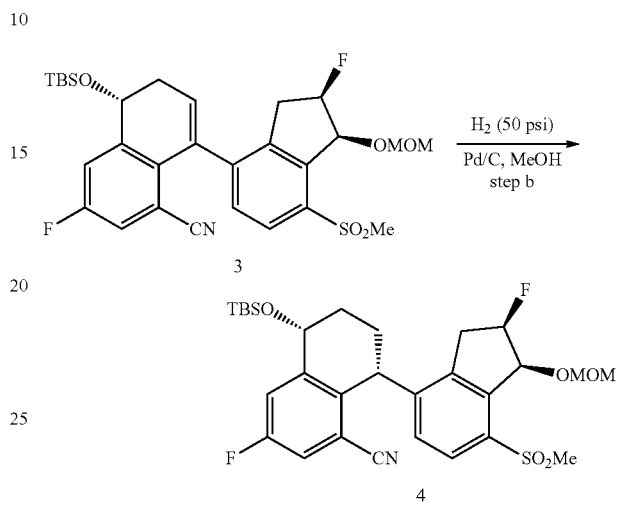

To a round-bottomed flask was charged with triflate 1 (139.4 g, 308.8 mmol, 1.0 equiv.), boronate 2 (136.0 g, 339.7 mmol, 1.1 equiv.), Pd(dppf)Cl$_2$ (11.3 g, 15.44 mmol, 0.05 equiv.), Na$_2$CO$_3$ (65.5 g, 617.6 mmol, 2.0 equiv.), 1,4-dioxane (1.2 L) and H$_2$O (0.4 L). The reaction mixture was degassed with N$_2$ bubbling for 10 min before it was stirred at 80° C. for 1 h. Upon completion, as shown by LCMS (MeCN/H$_2$O—20%→100%, 6 min), the reaction mixture was quenched with sat. sol. NaCl and extracted with EtOAc. The combined organic extract was washed with sat. sol. NaCl, dried over Na$_2$SO$_4$, filtered, and concentrated. The residue was purified using column chromatography on silica gel (Hexane/EtOAc—0%→40%, using two 750 g columns). The obtained orange foam was stirred with SilicaMetS dimercaptotriazine (160 g) and activated charcoal (40 g) in EtOAc (1 L, 0.3M) at 23° C. for 16 h. The solution was then filtered and concentrated to afford product 3 (151.8 g, 85%) as a yellow foam. $^1$H NMR (400 MHZ, Chloroform-d) δ 8.04-7.88 (m, 1H), 7.58-7.48 (m, 1H), 7.46-7.26 (m, 1H), 7.23-7.10 (m, 1H), 6.26-6.15 (m, 1H), 5.54-5.03 (m, 3H), 4.90-4.75 (m, 2H), 3.56-3.50 (m, 3H), 3.33-3.22 (m, 3.5H), 3.01-2.81 (m, 0.5H), 2.76-2.63 (m, 1H), 2.61-2.33 (m, 2H), 1.09-0.84 (m, 9H), 0.24-0.09 (m, 6H). ESI MS [M+Na]$^+$ for C$_{29}$H$_{35}$F$_2$NO$_5$SSi, calcd 598.2, found 598.3.

The treatment of the column chromatography purified product with a metal scavenger afforded sufficiently purified Compound 3 to give reproducible yields in the subsequent hydrogenation step (i.e., step b). In this preparation, the residual Pd content in the partially purified product from step a was found to have 4264 ppm Pd as determined by Inductively Coupled Plasma Optical Emission Spectrometry (ICP—OES). Under conditions of the subsequent hydrogenation step (i.e., step b), the partially purified product resulted in sluggish reaction times, poor reproducibility, and/or a substantial amount of side reactions. However, the use of SiliaMetS Thiol or SiliaMetS dimercaptotriazine (DMT) heavy metal scavengers reduced the residual Pd content from 4264 ppm to 378 ppm and 316 ppm, respectively, which permitted reproducible hydrogenation for the further purified product from step a under conditions described below.

Product 3 of step a (151.5 g, 263.1 mmol, 1.0 equiv.) was dissolved in MeOH (1.25 L, 0.2 M) under nitrogen, and Pd/C (30.3 g, 20 wt %, 10% Pd) was added to the reaction vessel. The mixture was shaken in a Parr shaker apparatus under an atmosphere of H$_2$ (50 psi) for 3 h. Upon completion as shown by $^{19}$F and $^1$H NMR, Celite and EtOAc were added to the reaction vessel, and the solution was stirred vigorously for 10 min. The mixture was then filtered through Celite, washed with EtOAc (3 times), and concentrated to afford a dark grey solid. The solid was then triturated with MeOH (300 mL), filtered, and washed twice with additional MeOH to afford product 4 as a light grey solid (101.6 g, 67%; 57% over two steps). $^1$H NMR (400 MHZ, Chloroform-d) δ 7.76 (d, J=8.2 Hz, 1H), 7.47 (d, J=9.4 Hz, 1H), 7.22 (ddd, J=7.6, 2.8, 0.6 Hz, 1H), 6.63 (br. s, 1H), 5.60-5.30 (m, 2H), 5.10 (d, J=6.5 Hz, 1H), 4.85 (d, J=6.8 Hz, 1H), 4.76 (dd, J=9.2, 5.2 Hz, 1H), 4.54 (br. s, 1H), 3.73-3.55 (m, 1H), 3.51 (s, 3H), 3.27 (s, 3H), 3.18-2.95 (m, 1H), 2.26-2.15 (m, 1H), 1.93-1.66 (m, 3H), 0.94 (s, 9H), 0.20 (s, 3H), 0.13 (s, 3H). ESI MS [M+Na]$^+$ for C$_{29}$H$_{37}$F$_2$NO$_5$SSi, calcd 600.2, found 600.3.

Step c: Synthesis of Compound 5

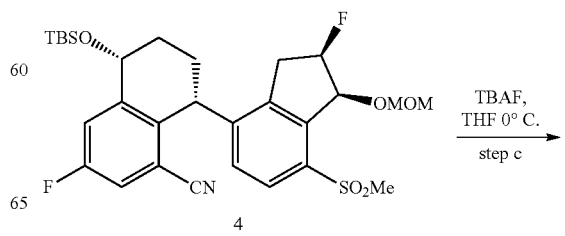

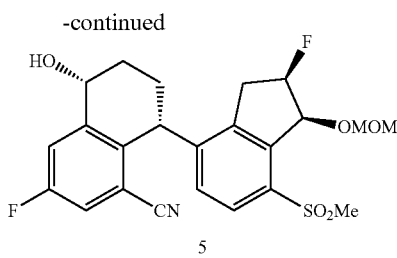

5

TBAF (712.5 mL, 1M in THF, 712.5 mmol, 1.5 equiv.) was added over 10 min to a solution of product 4 of step b (274.4 g, 475.0 mmol, 1.0 equiv.) in THF (2.2 L) at 0° C. After the addition, the reaction was analyzed by LC/MS (MeCN/H$_2$O—20%→100%, 6 min), and upon completion it was partitioned between EtOAc and H$_2$O. The solution was extracted with EtOAc, and the combined organic extract was washed with sat. sol. NaCl, dried over Na$_2$SO$_4$, filtered, and concentrated. The crude product 5 was used in the next step without further purification. $^1$H NMR (400 MHZ, Chloroform-d) δ 7.70 (d, J=8.0 Hz, 2H), 7.24 (ddd, J=7.5, 2.8, 0.7 Hz, 1H), 6.59 (br. s, 1H), 5.59-5.33 (m, 2H), 5.09 (dd, J=6.9, 0.8 Hz, 1H), 4.85 (d, J=6.8 Hz, 1H), 4.79 (dd, J=10.3, 5.9 Hz, 1H), 4.57 (d, J=5.6 Hz, 1H), 3.65-3.54 (m, 1H), 3.51 (s, 3H), 3.26 (s, 3H), 3.19-2.93 (m, 1H), 2.50 (br. s, 1H), 2.32-2.12 (m, 1H), 2.01-1.91 (m, 1H), 1.86-1.74 (m, 1H), 1.74-1.59 (m, 1H). ESI MS [M+Na]$^+$ for C$_{23}$H$_{23}$F$_2$NO$_5$S, calcd 486.1, found 486.0.

Step d: Synthesis of Compound 6

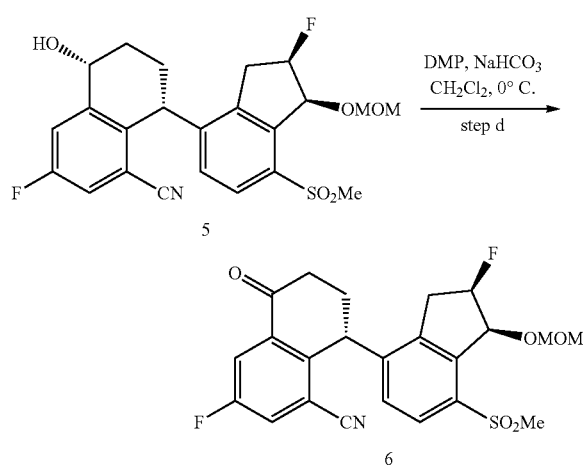

To a suspension of product 5 from step c (475.0 mmol, 1.0 equiv.) and NaHCO$_3$ (43.9 g, 522.5 mmol, 1.1 equiv.) in CH$_2$Cl$_2$ (2.4 L, 0.2M) at 0° C. was added DMP (221.6 g, 522.5 mmol, 1.1 equiv.) slowly in portions. The reaction was stirred for 30 min and was analyzed by LC/MS (MeCN/H$_2$O—20%→100%, 6 min). Upon completion, as shown by LC/MS and 1H NMR, the reaction was quenched by addition of saturated sol. NaHCO$_3$ (0.7 L) and saturated sol. Na$_2$S$_2$O$_3$ (0.7 L). Celite was added and the solution was stirred for 20 min before it was filtered over Celite. The layers were separated, and the aqueous layer was back extracted with CH$_2$Cl$_2$ twice. The combined organic extract was washed with saturated sol. Na$_2$S$_2$O$_3$, then dried over Na$_2$SO$_4$, filtered, and concentrated to dryness. This product was used in the next step without further purification. $^1$H NMR (400 MHZ, Chloroform-d) δ 8.08 (dd, J=8.6, 2.6 Hz, 1H), 7.76 (d, J=8.1 Hz, 1H), 7.57 (dd, J=7.2, 2.8 Hz, 1H), 6.57 (d, J=8.0 Hz, 1H), 5.62-5.31 (m, 2H), 5.11 (dd, J=6.9, 0.8 Hz, 1H), 4.88-4.83 (m, 2H), 3.65 (dd, J=22.5, 17.2 Hz, 1H), 3.53 (s, 3H), 3.28 (s, 3H), 3.14 (ddd, J=32.8, 17.1, 4.6 Hz, 1H), 2.70-2.44 (m, 3H), 2.16-2.06 (m, 1H). ESI MS [M+Na]$^+$ for C$_{23}$H$_{21}$F$_2$NO$_5$S, calcd 484.1, found 484.0.

Step e: Synthesis of Compound 7

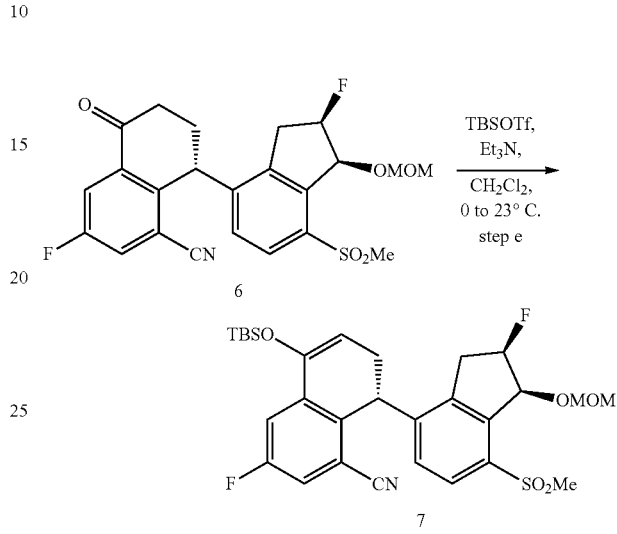

Product 6 of step d (475.0 mmol, 1.0 equiv.) was dissolved in CH$_2$Cl$_2$ (2.4 L, 0.2M) and the reaction mixture was cooled to 0° C. Et$_3$N (463 mL, 3325 mmol, 7.0 equiv.) was then added followed by TBSOTf (382 mL, 1662 mmol, 3.5 equiv.) which was added dropwise over 15 min. The mixture was stirred for 16 h at 23° C. and then analyzed by LC/MS (MeCN/H$_2$O—20%→100%, 6 min). Upon completion, the reaction mixture was cooled in an ice-bath and quenched with sat. sol. NaHCO$_3$ and extracted with CH$_2$Cl$_2$ twice. The combined organic extract was washed with sat. sol. NaCl, dried over Na$_2$SO$_4$, filtered, and concentrated. The residue was purified using column chromatography on silica gel (Hexane/EtOAc—0%→50%, using three 750 g columns) to afford product 7 (234 g, 86% over 3 steps) as a slightly yellow foam. $^1$H NMR (400 MHZ, Chloroform-d) δ 7.67 (d, J=8.1 Hz, 1H), 7.55 (dd, J=9.4, 2.7 Hz, 1H), 7.19 (dd, J=7.7, 2.7 Hz, 1H), 6.68 (d, J=8.2 Hz, 1H), 5.57-5.32 (m, 2H), 5.09 (dd, J=6.9, 0.7 Hz, 1H), 4.94 (dd, J=7.0, 2.5 Hz, 1H), 4.85 (d, J=6.8 Hz, 1H), 4.60 (d, J=8.1 Hz, 1H), 3.66 (dd, J=22.4, 17.1 Hz, 1H), 3.51 (s, 3H), 3.24 (s, 3H), 3.22-3.10 (m, 1H), 3.11-2.97 (m, 1H), 2.26 (ddd, J=17.1, 6.9, 1.3 Hz, 1H), 1.00 (s, 9H), 0.19 (s, 3H), 0.15 (s, 3H). ESI MS [M+Na]$^+$ for C$_{29}$H$_{35}$F$_2$NO$_5$SSi, calcd 598.19, found 598.0.

Step f: Synthesis of Compound 8

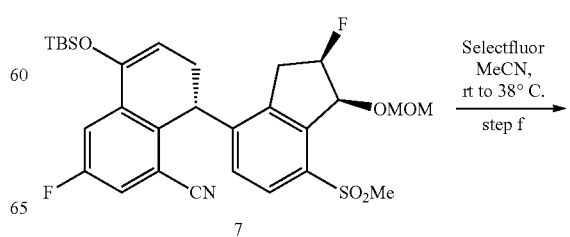

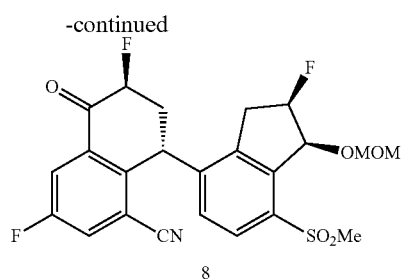

Product 7 of step e (234.0 g, 406.4 mmol, 1.0 equiv.) was dissolved in MeCN (2.0 L, 0.2M) at 23° C. and SelectFluor (288 g, 812.9 mmol, 2.0 equiv.) was added slowly over 15 min. During the course of the addition, the internal temperature rose to 38° C. The mixture was then stirred for an additional 15 min at 40° C., when complete conversion was observed by LC/MS (MeCN/H$_2$O—20%→100%, 6 min). The reaction mixture was then quenched at 0° C. with sat. sol. NaHCO$_3$ and extracted with EtOAc twice. The combined organic extract was washed water and then with sat. sol. NaCl, dried over Na$_2$SO$_4$, filtered, and concentrated. The crude product 8 was used in the next step without further purification. $^1$H and $^{19}$F NMR showed a diastereoselectivity ratio of >20:1. $^1$H NMR (400 MHZ, Chloroform-d) δ 8.11 (dd, J=8.0, 2.8 Hz, 1H), 7.78 (d, J=8.1 Hz, 1H), 7.63 (dd, J=7.1, 2.8 Hz, 1H), 6.52 (d, J=8.1 Hz, 1H), 5.64-5.35 (m, 2H), 5.26-5.06 (m, 2H), 5.04-4.95 (m, 1H), 4.87 (d, J=6.9 Hz, 1H), 3.62 (dd, J=22.3, 17.1 Hz, 1H), 3.53 (s, 3H), 3.28 (s, 3H), 3.18 (ddd, J=33.5, 17.3, 4.7 Hz, 1H), 2.79 (tt, J=13.1, 6.4 Hz, 1H), 2.51 (dddd, J=12.6, 7.5, 5.4, 2.4 Hz, 1H). ESI MS [M+Na]$^+$ for C$_{23}$H$_{20}$F$_3$NO$_5$S, calcd 502.1, found 502.1.

Step g: Synthesis of Compound 9

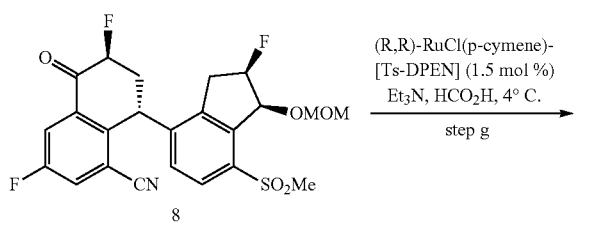

Product 8 of step f (108.4 mmol, 1.0 equiv.) was dissolved in CH$_2$Cl$_2$ (540 mL, 0.2M) and cooled to 0° C. Et$_3$N (30.2 mL, 216.8 mmol, 2.0 equiv.) and HCO$_2$H (12.3 mL, 326.4 mmol, 3.0 equiv.) were then added and the solution was degassed for 10 min. When the internal temperature of the reaction reached 0° C., RuCl(p-cymene)[(R,R)-Ts-DPEN] (1.03 g, 1.63 mmol, 0.015 equiv.) was added. A septum, a balloon, and a bubbler were attached to the flask, and the reaction was stirred at 4° C. for 16 h. Upon completion, as shown by LC/MS (MeCN/H$_2$O—20%→100%, 6 min) and 1H/19F NMR, the reaction mixture was poured into a sat. sol. NaHCO$_3$ and extracted with CH$_2$Cl$_2$. The combined organic extract was washed with sat. sol. NaCl, dried over Na$_2$SO$_4$, filtered, and concentrated. The residue was purified using column chromatography on silica gel (EtOAc/CH$_2$Cl$_2$—20%→80%, using a 750 g column) to afford the desired trans-isomer 9 (41.0 g, 79% over 2 steps) as a white solid. $^1$H NMR (400 MHZ, Chloroform-d) δ 7.80-7.68 (m, 2H), 7.31 (ddd, J=7.4, 2.8, 0.7 Hz, 1H), 6.48 (s, 1H), 5.63-5.35 (m, 2H), 5.11 (dd, J=6.9, 0.7 Hz, 1H), 4.94-4.80 (m, 2H), 4.79-4.73 (m, 1H), 4.71-4.46 (m, 1H), 3.73-3.46 (m, 4H), 3.28 (s, 3H), 3.08 (d, J=4.5 Hz, 1H), 2.48-2.32 (m, 1H), 2.14-2.06 (m, 1H). ESI MS [M+Na]$^+$ for C$_{23}$H$_{22}$F$_3$NO$_5$S, calcd 504.1, found 504.0.

Step h: Synthesis of Compound 10

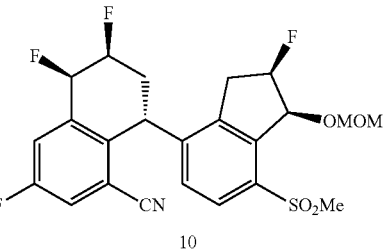

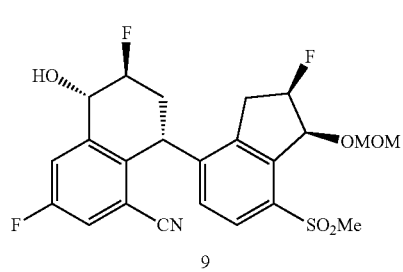

Product 9 of step g (41.0 g, 85.15 mmol, 1.0 equiv.) was dissolved in CH$_2$Cl$_2$ (850 mL) and the solution was cooled to an internal temperature of −40° C. (acetone bath with desired amount of dry ice) under an atmosphere of nitrogen. Diethylaminosulfur trifluoride (DAST) (56.3 mL, 425.76 mmol, 5.0 equiv.) was then added dropwise over 25 min at −40° C. The reaction mixture was slowly warmed from −40° C. to −10° C. over a period of 4 h. After this time, the reaction reached completion as shown by 1H/19F NMR, and the solution was poured in an ice-cold sat. sol. NaHCO$_3$. The layers were separated, and the aqueous layer was extracted with CH$_2$Cl$_2$. The combined organic extract was washed with sat. sol. NaCl, dried over Na$_2$SO$_4$, filtered, and concentrated. The residue was used in the next step without further purification. The cis/trans diastereomeric ratio was 12:1. $^1$H NMR (400 MHZ, Chloroform-d) δ 7.77 (d, J=8.1 Hz, 1H), 7.57 (dd, J=8.2, 2.8 Hz, 1H), 7.42 (ddd, J=7.4, 2.8, 1.1 Hz, 1H), 6.54 (d, J=8.1 Hz, 1H), 5.67 (ddd, J=50.6, 15.2, 2.7 Hz, 1H), 5.54-5.32 (m, 2H), 5.22-4.95 (m, 2H), 4.85 (d, J=6.8 Hz, 1H), 4.80 (t, J=6.4 Hz, 1H), 3.62-3.43 (m, 4H), 3.28 (s, 3H), 3.01 (ddd, J=32.8, 17.1, 4.6 Hz, 1H), 2.88-2.69 (m, 1H), 1.95-1.77 (m, 1H). ESI MS [M+Na]$^+$ for $C_{23}H_{21}F_4NO_4S$, calcd 506.1, found 506.2.

The diastereoselectivity of the transformation was improved to 20:1 by replacing DAST with bis(2-methoxyethyl)aminosulfur trifluoride (Deoxo-Fluor®) in the presence of 4-(trimethylsilyl) morpholine as described below.

Step h': Alternative Synthesis of Compound 10

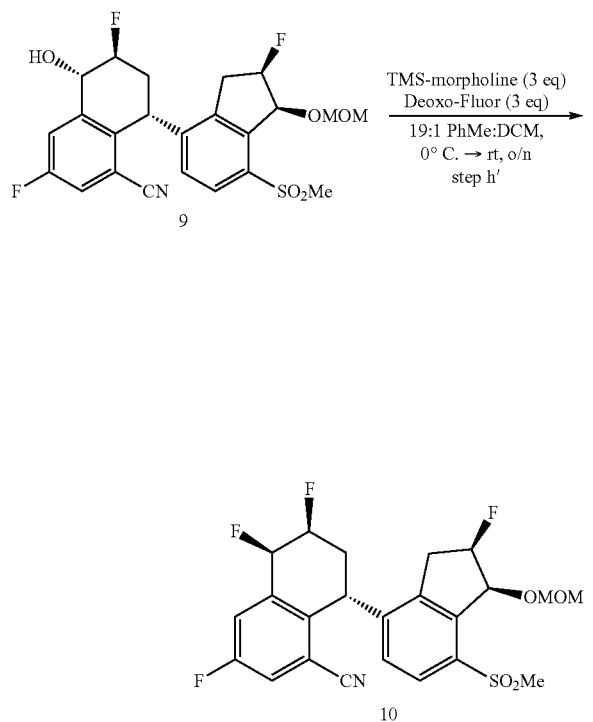

A 100 mL RBF equipped with a stir bar was charged with toluene (10 mL) and a solution of Deoxo-Fluor (2.7 M in PhMe, 2.31 mL, 6.24 mmol, 3 eq) was added. The mixture was cooled to 0° C. in an ice bath and TMS-morpholine (1.11 mL, 6.24 mmol, 3 eq) was added dropwise over ~5 minutes. The ice bath was subsequently removed, and the mixture was warmed to room temperature over 2 hours, during which it became increasingly heterogeneous and a white precipitate formed. After 2 hours, the suspension was diluted with toluene (28 mL) and was again cooled to 0° C. in an ice bath. The fluorohydrin (1.00 g, 2.08 mmol, 1 eq) in DCM (2 mL, ~0.05 M total) was then added dropwise over ~5 minutes and the reaction was warmed to room temperature overnight. Upon completion, the reaction was quenched with satd. NaHCO$_3$ (~50 mL) and diluted with EtOAc (~25 mL). The organic layer was separated, and the aqueous layer was extracted with EtOAc (~50 mL). The combined organic layers were washed with 1 M HCl (~50 mL), dried with Na$_2$SO$_4$, filtered, and concentrated to give the crude cis-difluoride (1.06 g, 93% crude, >20:1 dr).

Step i: Synthesis of Compound 11

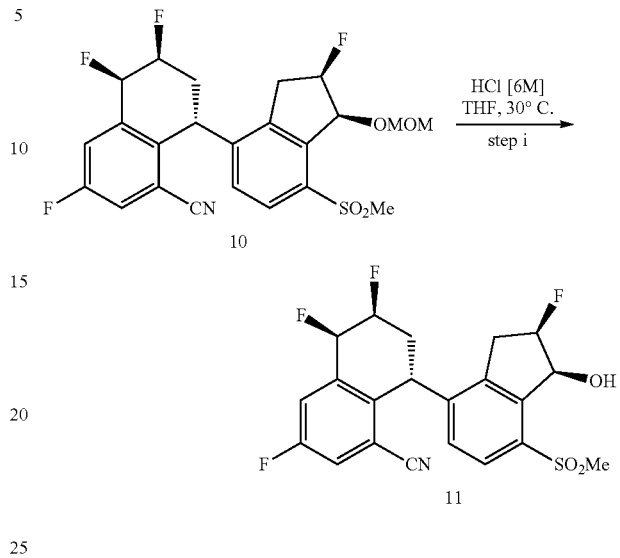

Product 10 of step h (37.85 g, 78.28 mmol, 1.0 equiv.) was dissolved in THF (400 mL) at 23° C. A solution of hydrochloric acid (320 mL, 6M) was added dropwise over 20 min, and the mixture was stirred at 30° C. for 4 h. After this time, the reaction reached completion, as shown by LC/MS (MeCN/H$_2$O—20%→100%, 6 min). The reaction mixture was diluted with water (1 L) and EtOAc (0.6 L), back-extracted twice with EtOAc, and washed with water, sat. sol. NaHCO$_3$, and brine. The organic layer was dried over Na$_2$SO$_4$, filtered, and concentrated. The material (32.25 g, 94%) was triturated with CH$_2$Cl$_2$ (45 mL) at 45° C., filtered, and washed with a minimum of cold CH$_2$Cl$_2$ and cold hexanes to afford 11 as a white crystalline solid (26.15 g, 76%, 12:1 dr). $^1$H NMR (400 MHZ, DMSO-d$_6$) δ 7.96 (ddd, J=8.3, 2.7, 1.3 Hz, 1H), 7.89 (dd, J=8.9, 2.7 Hz, 1H), 7.57 (d, J=8.1 Hz, 1H), 6.66 (d, J=8.1 Hz, 1H), 5.95 (ddd, J=51.2, 13.5, 2.2 Hz, 1H), 5.89 (d, J=5.6 Hz, 1H), 5.47 (ddd, J=10.0, 6.2, 4.9 Hz, 1H), 5.26 (qd, J=52.5, 5.4 Hz, 1H), 5.12 (tddd, J=47.4, 18.7, 10.3, 2.7 Hz, 1H), 4.83 (t, J=5.4 Hz, 1H), 3.30 (s, 3H), 3.28-3.13 (m, 2H), 2.71-2.60 (m, 1H), 2.02-1.85 (m, 1H). $^{19}$F NMR (376 MHZ, DMSO-d$_6$) δ −112.3, −179.6, −196.7, −199.4. ESI MS [M+Na]$^+$ for $C_{21}H_{17}F_4NO_3SNa$, calcd 462.0, found 461.9.

Example 3: Hydrogenation of Compound 8

The formation of trans-isomer 9 from step g of Example 2 as the major product was not expected based on prior reports that indicated formation of the cis-isomer was favored for ruthenium-catalyzed asymmetric hydrogenation of cyclic ketones. See, e.g., Touge et al., Org. Lett. 2021, 23, 3070-3075; Betancourt, R. M. et al., J. Org. Chem. 2021, 86, 12054-12063; and Ros et al. Org. Lett. 2006, 8, 1, 127-130.

Accordingly, asymmetric hydrogenation of compound 8 catalyzed by the isomeric RuCl(p-cymene)[(S,S)-Ts-DPEN] catalyst, and hydrogenation using non-chiral hydrogen sources, were investigated. Potential products of the hydrogenation reactions for these experiments are summarized below.

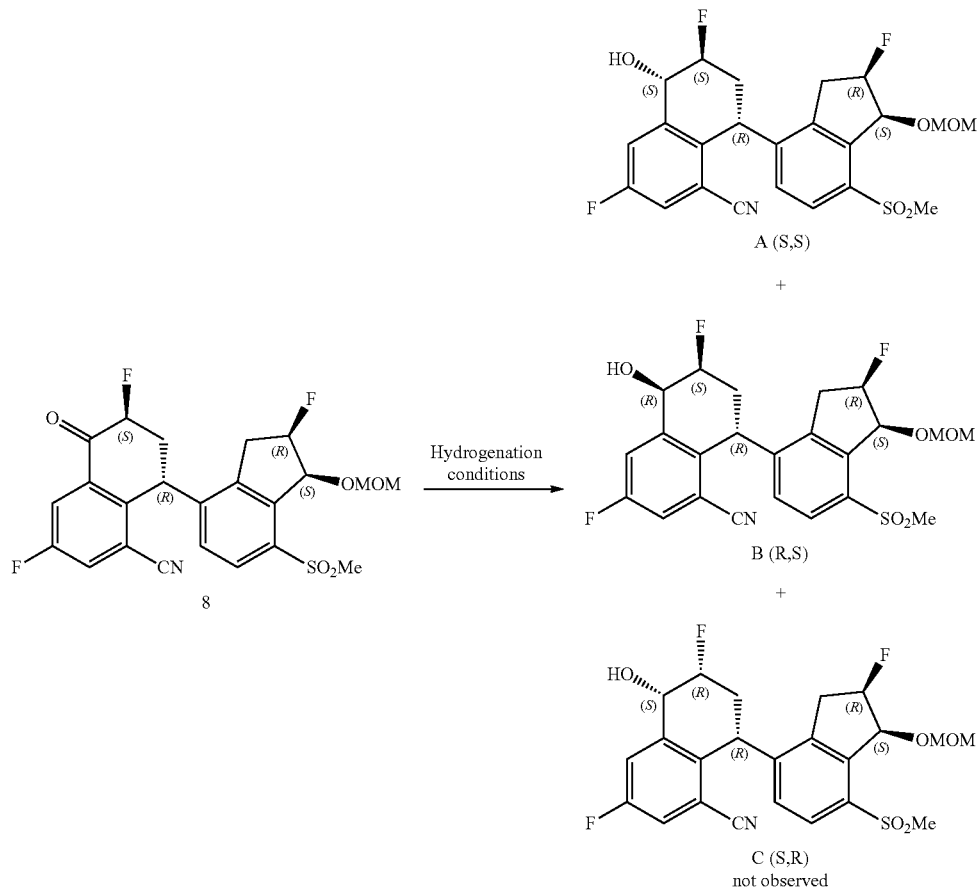

TABLE 1

Effect of Hydrogenation Conditions on Stereochemistry

| Entry | Hydrogenation Conditions | Yield | Results |
|---|---|---|---|
| 1 | RuCl(p-cymene)[(R,R)-Ts-DPEN], Et$_3$N, HCO$_2$H, 0° C., 16 h | 82% | A:B = 20:1 |
| 2 | RuCl(p-cymene)[(S,S)-Ts-DPEN], Et$_3$N, HCO$_2$H, 0° C., 16 h | 83% | A:B = 1:6 |
| 3 | NaBH$_4$, THF, MeOH, 0° C., 1 h | 84% | A:B = 2:1 |

The results of the experiments are summarized in Table 1 above. For the ruthenium catalyzed hydrogenation reactions, the reactions were performed according to the procedure described for Step g of Example 2. For Entry 3, compound 8 (40 mg, 0.083 mmol, 1.0 equiv.) was dissolved in a THF/MeOH mixture (1.6 mL, 1:1, v/v) and cooled to 0° C. Once cooled, NaBH$_4$ (6 mg, 0.167 mmol, 2.0 equiv.) was added, and the mixture was allowed to stir at 0° C. for 1 h. The reaction mixture was then poured into sat. sol. NaHCO$_3$ and extracted with CH$_2$Cl$_2$. The organic layer was washed with brine, dried over Na$_2$SO$_4$, filtered, and concentrated. The mixture was purified by chromatography (Hexane/EtOAc—0%→55%) to afford the desired product. Characterization of Isomer A (trans-isomer 9) can be found in step g of Example 2 above. Characterization of Isomer B (cis-isomer 9): $^1$H NMR (400 MHZ, CDCl$_3$) δ 7.78 (d, J=8.1 Hz, 1H), 7.65 (ddd, J=8.7, 2.7, 0.6 Hz, 1H), 7.34 (dd, J=7.5, 2.8 Hz, 1H), 6.63 (d, J=8.1 Hz, 1H), 5.51-5.33 (m, 2H), 5.10 (dd, J=6.9, 0.7 Hz, 1H), 5.09-4.94 (m, 1H), 4.94-4.88 (m, 1H), 4.85 (d, J=6.9 Hz, 1H), 4.74 (t, J=6.7 Hz, 1H), 3.52 (s, 3H), 3.51-3.42 (m, 1H), 3.28 (s, 3H), 2.97 (ddd, J=32.8, 17.2, 4.6 Hz, 1H), 2.81-2.69 (m, 1H), 2.52 (dd, J=7.1, 2.6 Hz, 1H), 1.83 (dddd, J=28.4, 14.1, 6.3, 2.5 Hz, 1H). 19F NMR (376 MHz, CDCl$_3$) δ −111.0, −194.5, −202.0. ESI MS [M+Na]$^+$ for C$_{23}$H$_{22}$F$_3$NNaO$_5$S, calcd 504.1, found 504.0.

The results suggested that the stereochemistry of the α-fluoro group of the tetralone moiety of compound 8 affected the stereochemical outcome of ruthenium catalyzed hydrogenation reaction. Without wishing to be bound by theory, the α-fluoro group of compound 8 may resist dynamic kinetic resolution to give the trans-isomer as the major product when the hydrogenation was catalyzed by RuCl(p-cymene)[(R,R)-Ts-DPEN] under the conditions described herein.

Example 3: Single Crystal X-ray Diffraction Studies of Compounds 8, 9, and 11

The stereochemistry of compounds 8, 9 and 11 was confirmed by single crystal X-ray diffraction.

Single crystal X-ray diffraction studies were carried out on a Bruker Microstar APEX II CCD (compound 8) or Bruker Smart APEX II CCD (compounds 9 and 11) diffractometer equipped with Cu Kα radiation (1=1.54178 Å).

Compound 8

Crystals of compound 8 were grown from DCE/Pentane. A 0.15×0.05×0.02 mm piece of a colorless crystal was mounted on a Cryoloop with Paratone oil. Data were collected in a nitrogen gas stream at 100(2) K using f and v scans. Crystal-to-detector distance was 40 mm and exposure time was 10, 15, 50, 55, or 60 seconds depending on the 2q range per frame using a scan width of 1.25°. Data collection was 99.5% complete to 67.679° in q. A total of 31302 reflections were collected covering the indices, −20<=h<=20, −33<=k<=34, −10<=l<=9. 8017 reflections were found to be symmetry independent, with a $R_{int}$ of 0.1078. Indexing and unit cell refinement indicated a Primitive, Orthorhombic lattice. The space group was found to be $P2_12_12$. The data were integrated using the Bruker SAINT Software program and scaled using the SADABS software program. Solution by direct methods (SHELXT) produced a complete phasing model consistent with the proposed structure.

All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. Crystallographic data are summarized in Table 2. The ORTEP diagram is shown in FIG. 1.

TABLE 2

Crystal data and structure refinement for Compound 8.

| | |
|---|---|
| Empirical Formula | C23 H20 F3 N O5 S |
| Formula Weight | 479.46 |
| Temperature | 100K |
| Wavelength | 1.54178 Å |
| Crystal System | Orthorhombic |
| Space Group | $P2_12_12$ |
| Unit Cell Dimensions | a = 17.0354(7)Å    α = 90°. |
| | b = 28.5675(12) Å   β = 90°. |
| | c = 9.0984(3) Å    γ = 90°. |
| Volume | 4427.8(3) Å$^3$ |
| Z | 8 |
| Density (calculated) | 1.438 Mg/m$^3$ |
| Absorption Coefficient | 1.850 mm$^{-1}$ |
| F(000) | 1984 |
| Crystal Size | 0.15 × 0.05 × 0.02 mm$^3$ |
| Theta Range for Data Collection | 3.020 to 68.957°. |
| Index Ranges | −20 <= h <= 20, −33 <= k <= 34, −10 <= l <= 9 |
| Reflections Collected | 31302 |
| Independent Reflections | 8017 [R(int) = 0.1078] |
| Completeness of Theta = 67.679° | 99.5% |
| Absorption Correction | Semi-empirical from equivalents |
| Max. and Min. Transmission | 0.5212 and 0.3839 |
| Refinement Method | Full-matrix least-squares on F$^2$ |
| Data/Restraints/Parameters | 8017/12/623 |
| Goodness-of-fit on F$^2$ | 1.090 |
| Final R indices [I > 2sigma(I)] | R1 = 0.0967, wR2 = 0.2185 |
| R indices (all data) | R1= 0.1202, wR2 = 0.2305 |
| Absolute Structure Parameter | 0.081(17) |
| Largest diff. peak and hole | 0.457 and −0.464 e.Å$^{-3}$ |

Compound 9

Crystals of compound 9 were grown from DCM/Pentane. A 0.28×0.25×0.12 mm piece of a colorless crystal was mounted on a Cryoloop with Paratone oil. Data were collected in a nitrogen gas stream at 100(2) K using f and v scans. Crystal-to-detector distance was 40 mm and exposure time was 4, 10, or 20 seconds depending on the 2q range per frame using a scan width of 1.25°. Data collection was 99.7% complete to 67.679° in q. A total of 26157 reflections were collected covering the indices, −12<=h<=21, −12<=k<=11, −17<=l<=17. 4703 reflections were found to be symmetry independent, with a $R_{int}$ of 0.0641. Indexing and unit cell refinement indicated a Primitive, Orthorhombic lattice. The space group was found to be $P2_12_12$. The data were integrated using the Bruker SAINT Software program and scaled using the SADABS software program. Solution by direct methods (SHELXT) produced a complete phasing model consistent with the proposed structure.

Figure 2:
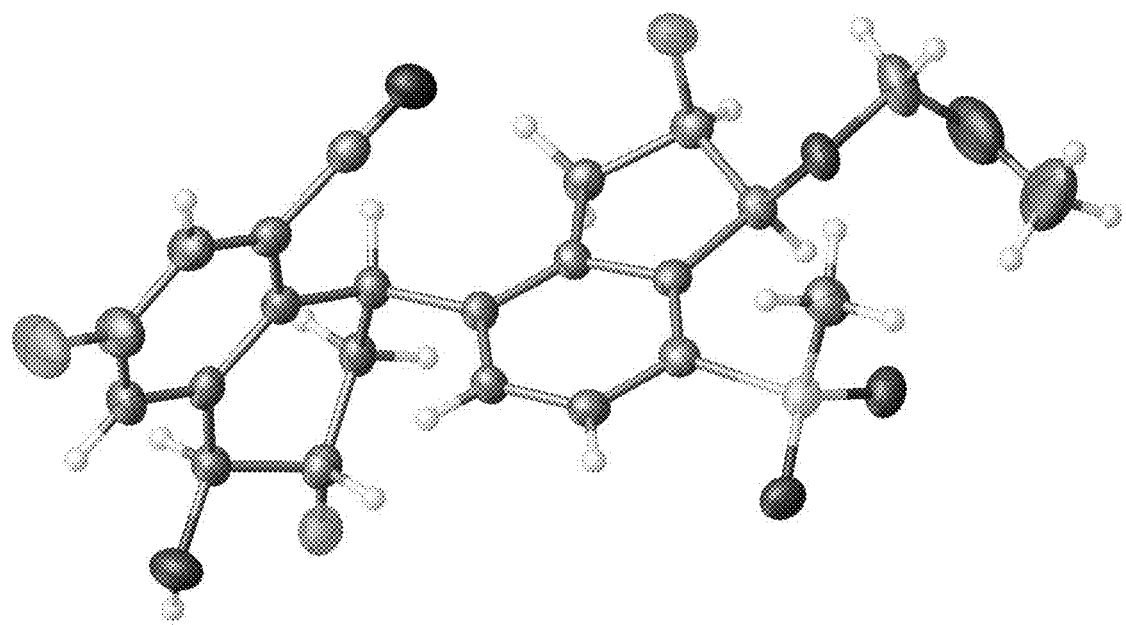
FIG. 2 shows an Oak Ridge Thermal Ellipsoid Plot (ORTEP) diagram of the single crystal x-ray diffraction pattern for Compound 9.

All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. Crystallographic data are summarized in Table 3. The ORTEP diagram is shown in FIG. 2.

TABLE 3

Crystal data and structure refinement for Compound 9.

| | |
|---|---|
| Empirical Formula | C23 H22 F3 N O5 S |
| Formula Weight | 481.47 |
| Temperature | 100.15K |
| Wavelength | 1.54178 Å |
| Crystal System | Orthorhombic |
| Space Group | $P2_12_12$ |
| Unit Cell Dimensions | a = 17.366(2) Å    α = 90°. |
| | b = 9.7099(12) Å   β = 90°. |
| | c = 14.3787(16) Å   γ = 90°. |
| Volume | 2424.6(5) Å$^3$ |
| Z | 4 |
| Density (calculated) | 1.319 Mg/m$^3$ |
| Absorption Coefficient | 1.689 mm$^{-1}$ |
| F(000) | 1000 |
| Crystal Size | 0.28 × 0.25 × 0.12 mm$^3$ |
| Theta Range for Data Collection | 3.073 to 73.708°. |
| Index Ranges | −12 <= h <= 21, −12 <= k <= 11, −17 <= l <= 17 |
| Reflections Collected | 26157 |
| Independent Reflections | 4703 [R(int) = 0.0641] |
| Completeness of Theta = 67.679° | 99.7% |
| Absorption Correction | Semi-empirical from equivalents |
| Max. and Min. Transmission | 0.5220 and 0.2696 |
| Refinement Method | Full-matrix least-squares on F$^2$ |
| Data/Restraints/Parameters | 4703/0/301 |
| Goodness-of-fit on F$^2$ | 1.066 |
| Final R indices [I > 2sigma(I)] | R1 = 0.0438, wR2 = 0.1132 |
| R indices (all data) | R1 = 0.0479, wR2 = 0.1234 |
| Absolute Structure Parameter | 0.058(11) |
| Largest diff. peak and hole | 0.358 and −0.380 e.Å$^{-3}$ |

Compound 11

Crystals of compound 11 were grown from DCM/Pentane. A 0.26×0.22×0.17 mm piece of a colorless crystal was mounted on a Cryoloop with Paratone oil. Data were collected in a nitrogen gas stream at 100(2) K using f and v scans. Crystal-to-detector distance was 40 mm and exposure time was 1, 3, or 5 seconds depending on the 2q range per frame using a scan width of 1.50°. Data collection was 100% complete to 67.679° in q. A total of 19643 reflections were collected covering the indices, −10<=h<=10, −11<=k<=11, −28<=l<=28. 3642 reflections were found to be symmetry independent, with a $R_{int}$ of 0.0384. Indexing and unit cell refinement indicated a Primitive, Orthorhombic lattice. The space group was found to be $P2_12_12_1$. The data were integrated using the Bruker SAINT Software program and scaled using the SADABS software program. Solution by direct methods (SHELXT) produced a complete phasing model consistent with the proposed structure.

Figure 3:
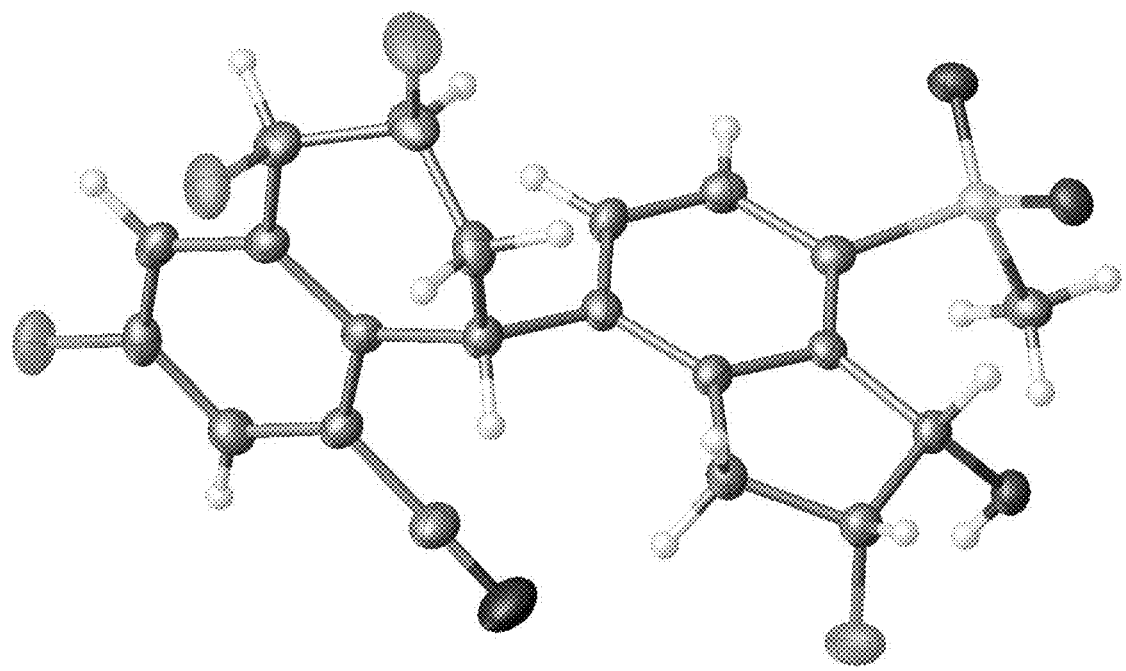
FIG. 3 shows an Oak Ridge Thermal Ellipsoid Plot (ORTEP) diagram of the single crystal x-ray diffraction pattern for Compound 11.

All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. Crystallographic data are summarized in Table 4. The ORTEP diagram is shown in FIG. 3.

TABLE 4

| Crystal data and structure refinement for Compound 11. | |
|---|---|
| Empirical Formula | C21 H17 F4 N O3 S |
| Formula Weight | 439.42 |
| Temperature | 100.0K |
| Wavelength | 1.54178 Å |
| Crystal System | Orthorhombic |
| Space Group | P2$_1$2$_1$2 |
| Unit Cell Dimensions | a = 8.7503(3) Å    α = 90°. |
|  | b = 9.2365(3) Å    β = 90°. |
|  | c = 23.7807(11) Å    γ = 90°. |
| Volume | 1922.01(13) Å$^3$ |
| Z | 4 |
| Density (calculated) | 1.519 Mg/m$^3$ |
| Absorption Coefficient | 2.070 mm$^{-1}$ |
| F(000) | 904 |
| Crystal Size | 0.26 × 0.22 × 0.17 mm$^3$ |
| Theta Range for Data Collection | 3.717 to 70.055°. |
| Index Ranges | −10 <= h <= 10, −11 <= k <= 11, |
|  | −28 <= l <= 28 |
| Reflections Collected | 19643 |
| Independent Reflections | 3642 [R(int) = 0.0384] |
| Completeness of Theta = 67.679° | 100.0% |
| Absorption Correction | Semi-empirical from equivalents |
| Max. and Min. Transmission | 0.5220 and 0.3487 |
| Refinement Method | Full-matrix least-squares on F$^2$ |
| Data/Restraints/Parameters | 3642/1/284 |
| Goodness-of-fit on F$^2$ | 1.093 |
| Final R indices [I > 2sigma(I)] | R1= 0.0316, wR2 = 0.0819 |
| R indices (all data) | R1 = 0.0319, wR2 = 0.0821 |
| Absolute Structure Parameter | −0.004(14) |
| Largest diff. peak and hole | 0.210 and −0.315 e.Å$^{-3}$ |

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process:

comprising contacting a compound of Formula (IIa)

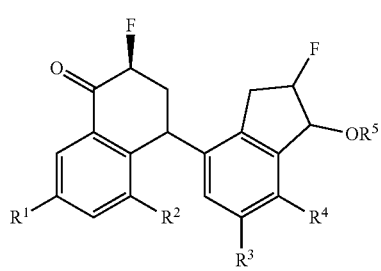

(IIa)

with a chiral ruthenium (II) catalyst and a hydrogen reagent;

thereby preparing a compound of Formula (Ia):

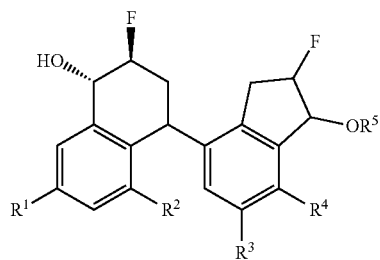

(Ia)

wherein the chiral ruthenium (II) catalyst is RuCl(p-cymene)[(R,R)-Ts-DPEN];

R$^1$ and R$^2$ are independently selected from —H, —F, —Cl, and —CN;

R$^3$ is —H, —F or —Cl;

R$^4$ is selected from —H, —F, —Cl, —C$_1$-C$_3$ alkyl, and —S(O)$_2$(C$_1$-C$_3$ alkyl), wherein the —C$_1$-C$_3$ alkyl or the —S(O)$_2$(C$_1$-C$_3$ alkyl) is optionally substituted with 1-3 halogen atoms;

R$^5$ is an alcohol protecting group; and the compound of Formula (Ia) has at least 90% diastereomeric purity.

2. The process of claim 1, wherein the hydrogen reagent is hydrogen gas or formic acid.

3. The process of claim 1, wherein the compound of Formula (Ia) is a compound of Formula (Ia-3):

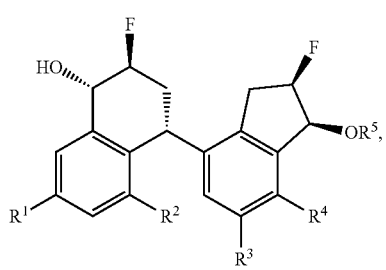

(Ia-3)

that is substantially free of other stereoisomers; and wherein the compound of Formula (IIa) is a compound of Formula (IIa-3):

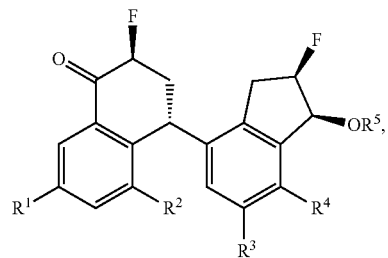

(IIa-3)

that is substantially free of other stereoisomers.

4. The process of claim 1, comprising contacting a compound of Formula (III):

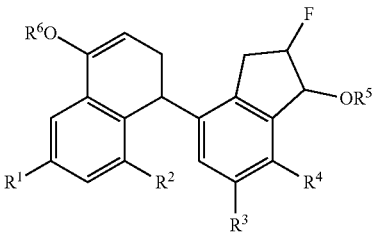

with an electrophilic fluorinating agent,
wherein R⁶ is an alcohol protecting group,
thereby preparing the compound of Formula (IIa).

5. The process of claim 4, wherein the electrophilic fluorinating agent is selected from 1-chloromethyl-4-fluoro-1,4-diazoniabicyclo[2.2.2]octane bis(tetrafluoroborate) (Selecfluor®), N-fluoro-N'-methyl-triethylenediamine bis(tetrafluoroborate) (Selectfluor® II), N-fluorobenzenesulfonamide (NFSI), 1,1'-difluoro-2,2'-bipyridinium bis(tetrafluoroborate) (Synfluor), 1-fluoropyridinium trifluoromethanesulfonate, and N-fluoropyridinium (NFPγ) salts including 1-fluoro-2,4,6-trimethylpyridinium tetrafluoroborate, 1-fluoro-2,3,4,5,6-pentachloropyridinium tetrafluoroborate, and 1-fluoro-2,6-dichloropyridinium tetrafluoroborate.

6. The process of claim 4, wherein the compound of Formula (III) is a compound of Formula (III-3):

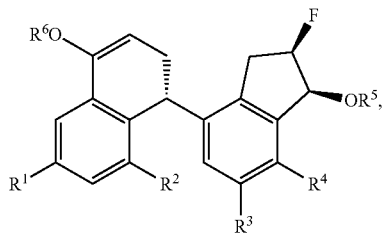

that is substantially free of other stereoisomers.

7. The process of claim 4, wherein R⁶ is trimethylsilyl (TMS), triethylsilyl (TES), triisopropylsilyl (TIPS), triphenylsilyl (TPS), or tert-butyldimethylsilyl (TBS).

8. The process of claim 4, comprising contacting a compound of Formula (IV):

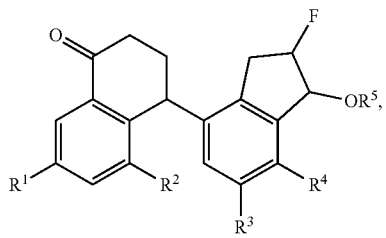

with a R⁶X reagent and a base, wherein
R⁶ is an alcohol protecting group,
X is —Cl, —Br, —I, -OMs, -OTs, or -OTf, and
the base is an amine, an amide, a carbonate, a phosphate, a tetra alkyl ammonium salt, or a hydroxide salt,
thereby preparing the compound of Formula (III).

9. The process of claim 8, wherein the compound of Formula (IV) is a compound of Formula (IV-3):

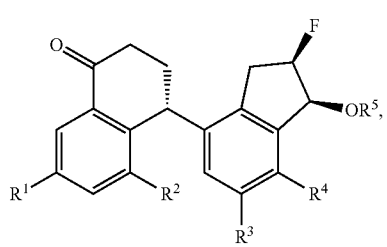

that is substantially free of other stereoisomers.

10. The process of claim 8, comprising preparing the compound of Formula (IV) by contacting a compound of Formula (V):

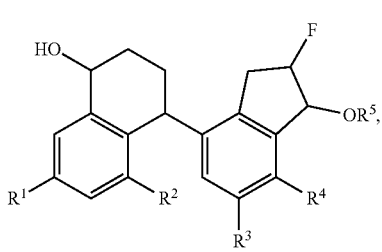

with an oxidizing agent,
thereby preparing the compound of Formula (IV).

11. The process of claim 10, wherein the oxidizing agent is selected from potassium permanganate, 1,1,1-tris(acetyloxy)-1,1-dihydro-1,2-benziodoxol-3-(1H)-one, 2-iodoxybenzoic acid, 1-acetoxy-5-bromo-1,2-benziodoxol-3(1H)-one, oxalyl chloride-dimethyl sulfoxide, tert-butyl hydroperoxide, sodium hypochlorite, and chromium (VI) trioxide.

12. The process of claim 10, wherein the compound of Formula (V) is a compound of Formula (V-3):

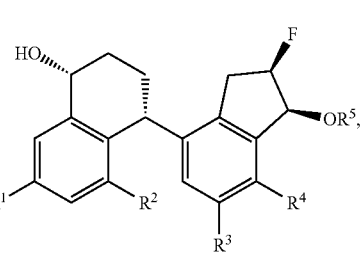

that is substantially free of other stereoisomers.

13. The process of claim 12, comprising preparing the compound of Formula (V), by:

(a) contacting a compound of Formula (VI):

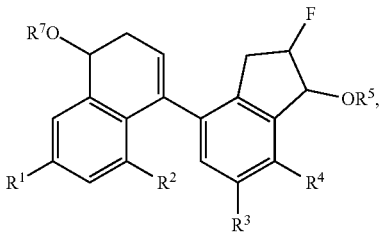

(VI)

wherein $R^7$ is an alcohol protecting group,
with a catalyst and a second hydrogen reagent to prepare a compound of Formula (VII):

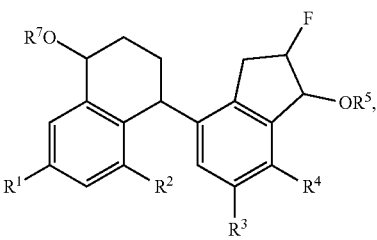

(VII)

wherein $R^7$ is an alcohol protecting group, and
(b) contacting the compound of Formula (VII) with a deprotecting agent, thereby preparing the compound of Formula (V).

14. The process of claim 13, wherein the catalyst is palladium on carbon.

15. The process of claim 14, wherein the compound of Formula (VI) comprises less than 1000 ppm palladium.

16. The process of claim 13, wherein the second hydrogen reagent is hydrogen gas or formic acid.

17. The process of claim 13, comprising preparing the compound of Formula (VI), the process comprising combining a compound of Formula (VIII):

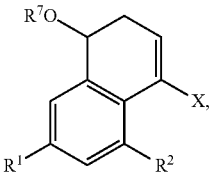

(VIII)

wherein X is —Br, —I, or -OTf;
with a compound of Formula (IX):

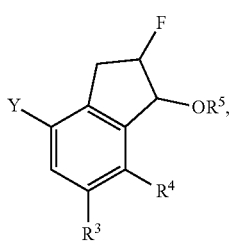

(IX)

wherein Y is —B(OH)$_2$, —B(OMe)$_2$, —B(OEt)$_2$, or -Bpin; and
a palladium catalyst;
to prepare the compound of Formula (VI).

18. The process of claim 17, wherein the palladium catalyst is Pd(dppe)Cl$_2$, Pd(dppp)Cl$_2$, Pd(dppf)Cl$_2$, Pd(PPh$_3$)$_2$Cl$_2$, or Pd(PPh$_3$)$_4$.

19. The process of claim 13, wherein $R^7$ is trimethylsilyl (TMS), triethylsilyl (TES), triisopropylsilyl (TIPS), triphenylsilyl (TPS), tert-butyldimethylsilyl (TBS), methoxymethyl (MOM), tetrahydropyranyl (THP), pivaloyl (Piv), tert-butoxycarbanyl (Boc), or trityl (Tr).

20. The process of claim 1, wherein $R^1$ is —F; $R^2$ is —CN; $R^3$ is —H; and/or $R^4$ is —S(O)$_2$CH$_3$.

21. The process of claim 1, wherein $R^5$ is methoxymethyl (MOM), 2-methoxyethoxymethyl (MEM), tetrahydropyranyl (THP), tert-butyl, allyl, benzyl, 2-methoxybenzyl, 3-methoxybenzyl, or 4-methoxybenzyl.

22. The process of claim 1, further comprising:
(a) contacting the compound of Formula (Ia):

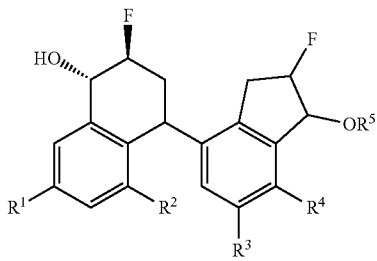

(Ia)

with a fluorinating agent to prepare a compound of Formula (XIa):

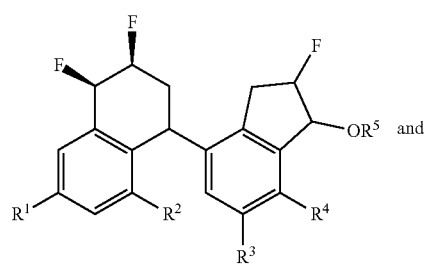

(XIa)

and (b) contacting the compound of Formula (XIa) with a second deprotecting agent, to prepare a compound of Formula (Xa):

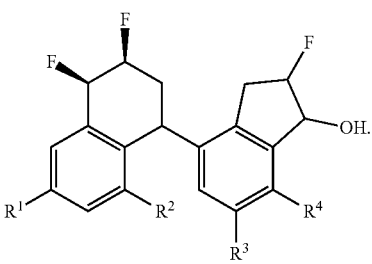

(Xa)

23. The process of claim 22, wherein the fluorinating agent is sulfur tetrafluoride, diethylaminosulfur trifluoride, [bis(2-methoxyethyl)amino]sulfur trifluoride, or N,N-diethyl-1,1,2,3,3,3-hexafluoropropylamine.

24. The process of claim 22, wherein the compound of Formula (Xa) is a compound of Formula (Xa-3):

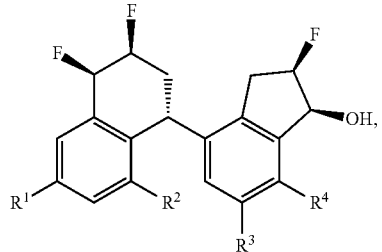

(Xa-3)

that is substantially free of other stereoisomers.

25. The process of claim 22, wherein the compound of Formula (Xa) has the structure:

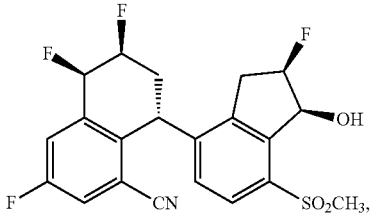 [SMILES: CS(=O)(=O)c1ccc([C@H]2C[C@H](F)[C@H](F)c3cc(F)cc(C#N)c32)c2c1[C@H](O)[C@H](F)C2]

that is substantially free of other stereoisomers.

* * * * *